(12) United States Patent
Hagen et al.

(10) Patent No.: US 6,872,358 B2
(45) Date of Patent: Mar. 29, 2005

(54) TEST STRIP DISPENSER

(75) Inventors: Robert Hagen, deceased, late of South Surrey (CA); by Colleen Hagen, legal representative, South Surrey (CA); Lorin P. Olson, Scotts Valley, CA (US); Robert J. Shartle, Livermore, CA (US)

(73) Assignee: LifeScan, Inc., Milpitas, CA (US)

( * ) Notice: Subject to any disclaimer, the term of this patent is extended or adjusted under 35 U.S.C. 154(b) by 275 days.

(21) Appl. No.: 10/052,212

(22) Filed: Jan. 16, 2002

(65) Prior Publication Data

US 2003/0133847 A1 Jul. 17, 2003

(51) Int. Cl.$^7$ .............................................. G01N 33/48
(52) U.S. Cl. ............................ 422/61; 422/58; 422/63; 436/43; 436/165
(58) Field of Search ........................... 422/58, 61, 102, 422/104, 63, 67; 436/43, 46, 165

(56) References Cited

U.S. PATENT DOCUMENTS

| | | |
|---|---|---|
| 2,641,358 A | 3/1950 | D.C. Santo |
| 3,393,831 A | 11/1966 | C.R. Stewart |
| 4,114,780 A | 9/1978 | Sharon |
| 4,187,077 A | 2/1980 | Covington et al. |
| RE30,895 E | 4/1982 | Butera |
| 4,464,552 A * | 8/1984 | Pawlowski .................. 206/569 |
| 4,717,018 A | 1/1988 | Sacherer et al. |
| 4,817,820 A | 4/1989 | Heiland |
| 4,911,344 A | 3/1990 | Kahler |
| 5,100,621 A * | 3/1992 | Berke et al. .................. 422/61 |
| 5,328,082 A | 7/1994 | Fritz et al. |
| 5,409,133 A | 4/1995 | Gringer |
| 5,426,032 A | 6/1995 | Phillips et al. |
| 5,489,414 A | 2/1996 | Schreiber et al. |
| 5,505,308 A * | 4/1996 | Eikmeier et al. ............ 206/449 |
| 5,510,266 A | 4/1996 | Bonner et al. |
| 5,534,224 A | 7/1996 | Abe |
| 5,542,567 A | 8/1996 | Julius |
| 5,575,403 A | 11/1996 | Charlton et al. |
| 5,630,986 A | 5/1997 | Charlton et al. |
| 5,736,103 A * | 4/1998 | Pugh .......................... 422/68.1 |
| 5,894,927 A | 4/1999 | Bennett |
| 5,971,941 A | 10/1999 | Simons et al. |
| 6,036,924 A | 3/2000 | Simons et al. |
| 6,534,017 B1 * | 3/2003 | Bottwein et al. ............ 422/104 |

FOREIGN PATENT DOCUMENTS

| | | |
|---|---|---|
| EP | 0 045 077 A | 2/1982 |
| FR | 2714895 | 7/1995 |
| WO | 94/10558 | * 11/1994 |
| WO | WO 98/47007 | 10/1998 |

* cited by examiner

Primary Examiner—Lyle A. Alexander
(74) Attorney, Agent, or Firm—Susan C. Tall; Carol M. LaSalle; Bozicevic, Field & Francis, LLP

(57) ABSTRACT

Devices for dispensing test strips and methods of using the same are provided. The subject devices are characterized by having a housing made of a cover and a base configured to retain a plurality of test strips. In certain embodiments, the height of the base is less than the height of each of the test strips, such that a portion of each of the test strips extends beyond the distal or top edge of the base. The subject devices may further be characterized as having a substantially air and moisture tight seal. In using the subject devices, a plurality of test strips stored in a subject device are provided. A single test strip is removed from the subject device by moving the test strip distal to the remaining test strips. Also provided by the subject invention are kits for use in practicing the subject methods.

14 Claims, 14 Drawing Sheets

PRIOR ART
COLORIMETRIC STRIP

PRIOR ART
ELECTROCHEMICAL STRIP

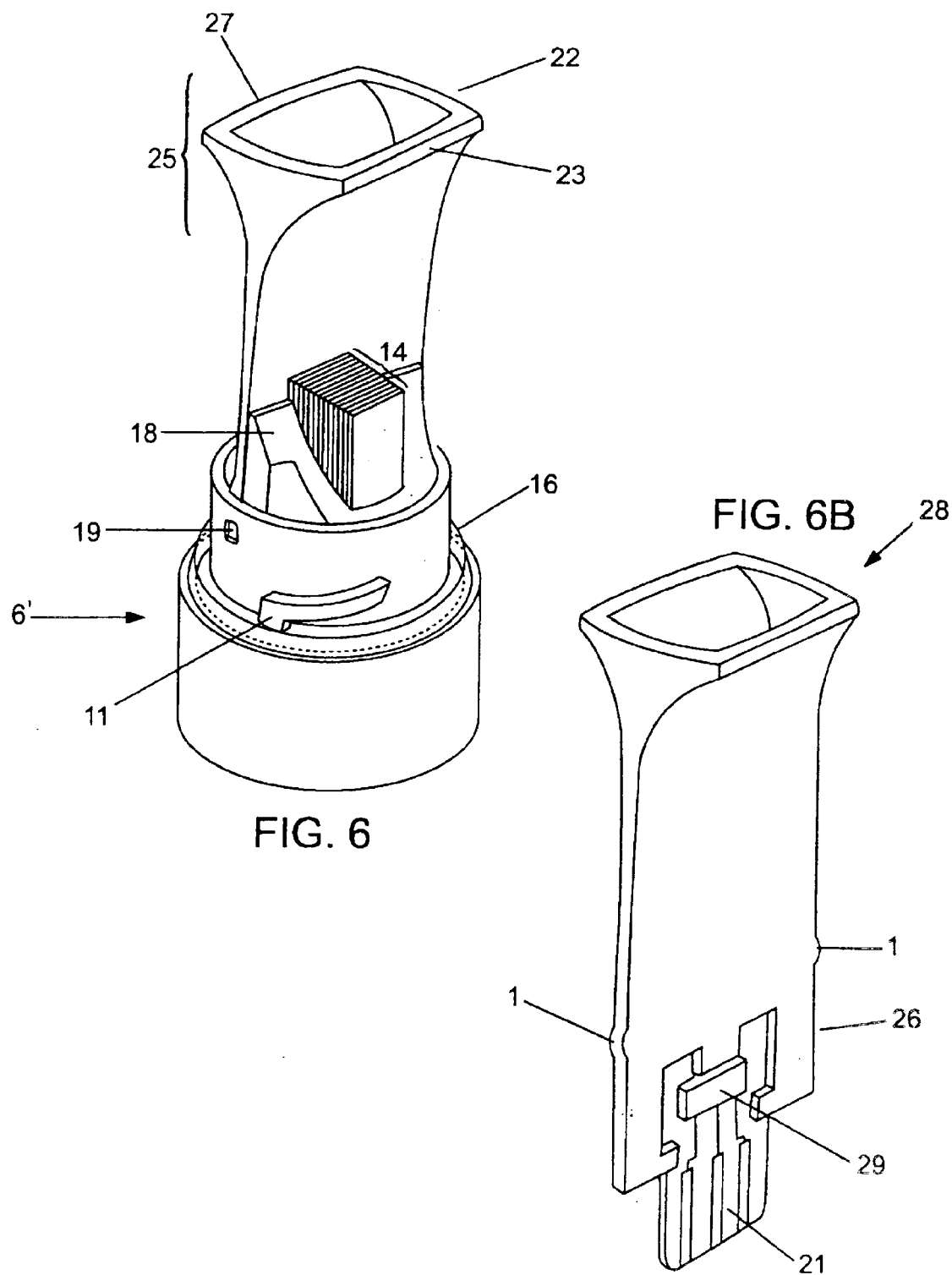

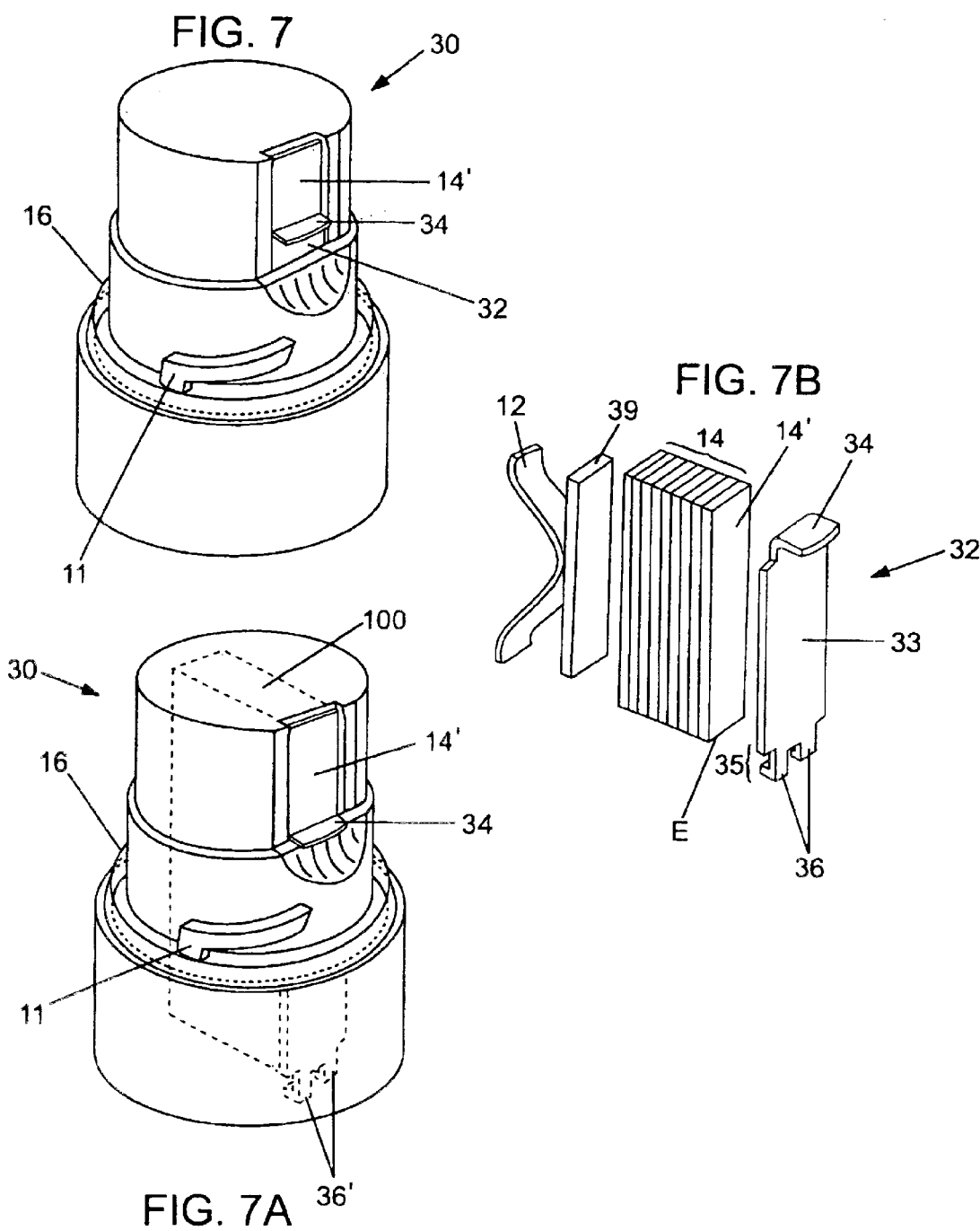

TEST STRIP DISPENSER

FIELD OF THE INVENTION

The field of this invention is test strip dispensers.

BACKGROUND OF THE INVENTION

Analyte concentration determination in physiological samples is of ever increasing importance to today's society. Such assays find use in a variety of application settings, including clinical laboratory testing, home testing, etc., where the results of such testing play a prominent role in the diagnosis and management of a variety of disease conditions. Analytes of interest include glucose for diabetes management, cholesterol for monitoring cardiovascular conditions, and the like. In response to this growing importance of analyte concentration determination, a variety of analyte concentration determination protocols and devices for both clinical and home testing have been developed.

Before testing can begin, an individual seeking to determine the presence and/or concentration of an analyte in a physiological sample must first obtain a test strip, apply a sample thereto and obtain the results, either manually or automatically with a meter or the like. However, obtaining a test strip to begin the procedure is not without difficulty. For example, diabetics typically have visual and/or dexterity problems, thus making the selection of a single test strip, which usually has a length of about 50 mm and a width of about 7 mm, from a plurality of such test strips difficult.

Typically, a plurality of test strips are stored in a relatively large vessel, i.e., a vessel large enough to hold a plurality of test strips and to completely encompass the test strips inside so as to protect the test strips from light, humidity, and other environmental contaminants including oils and the like from a user's hands, where such protection is necessary to insure the precision, accuracy and overall integrity of the test result. An exemplary embodiment of a subject test strip storage vessel is shown in FIG. 1. Thus, to obtain a single test strip from the vessel to begin a test, an individual has two options for removing a test strip. In one option, an individual may simply turn the vessel upside down to pour a test strip out. This, as is apparent, has significant disadvantages as the test strips stored inside the vessel may quickly spill onto out and becomes contaminated. In a second option, an individual places a finger inside the vessel to try to grasp a single test strip amongst a plurality of test strips without damaging any of the strips in the process. However, such a method oftentimes results in the user inadvertently contacting portions of the test strip that should not be touched, such as testing or reaction areas (i.e., areas on the strip having testing reagents, etc.) and the like, where such contact can impart contaminants and cause erroneous testing results. Similarly, other test strips may be inadvertently contacted resulting in erroneous testing results of those test strips as well.

Furthermore, the vessel must have a suitable shape and sized large enough to accommodate at least one finger therein, for easy removal of a test strip. In other words, the vessel must enable an individual, i.e., an individual who may be visually and dextrally impaired, to retrieve a test strip from amongst a plurality of test strips without damaging or contaminating any of such test strips.

However, it can be appreciated that the vessel, while maintaining a size large enough to serve its functions, must be small enough to enable portability of the vessel so that an individual may easily carry the vessel at all times to accommodate testing during the course of a day. However, due to the above described shape and size requirements, conventional vessels typically have a circular cross-sectional shape to accommodate insertion of at least one finger therein, have a height of about 60 mm and a diameter of about 25 mm and are commercially sold with about 25 test strips retained therein. As is apparent, such size and shape creates a great amount of unused space inside the vessel and minimizes the portability of the vessel. In other words, the vessels are larger than necessary to simply hold the test strips, thus increasing costs and decreasing portability.

U.S. Pat. No. 4,911,344 to Kahler discloses a strip dispenser box capable of dispensing a single test strip from a stack of test strips that does not require the user to insert a finger inside a vessel to retrieve a test strip. Rather, the '344 patent discloses a cap assembly with a strip feeder mechanism mounted to a housing having a magazine capable of holding a stack of test strips. The cap has a slot therein and a slide bar assembly slideably mounted in the slot for moving a test strip out of the dispenser, more particularly out of a gasket-sealed opening positioned on the cap assembly. However, the device disclosed in the '344 patent suffers from certain disadvantages. First and foremost, the strip dispenser of the '344 patent fails to maintain a completely moisture free environment. Specifically, at least two areas of the dispenser permit moisture to enter the housing and thus contact the test strips therein.

The first area which fails to provide a moisture free seal is the slot/slide bar assembly area. The slide bar is made of a cross shaped base member slideably positioned on the inner surface of the cap body and a finger grip which extends upward through the slot of the cap assembly. In operation, the finger grip is driven forward by the action of the thumb of the user and it carries a test strip out an opening of the cap assembly. As described in the patent, the preferred material of the dispenser is polyethylene plastic. In other words, both the cap assembly (the slot area) and the slide bar are made of polyethylene plastic. It will be apparent to one of skill in the art that such an assembly of two contacting polyethylene plastic surfaces cannot provide an adequate barrier to moisture.

The second area which fails to provide a moisture free seal is the opening through which a test strip is removed from the dispenser, even though a seal strip or gasket extends about ⅓₂ of an inch into the dispenser and covers the opening thereto. In other words, a gasket or the like is attached on a first side to the cap assembly and unattached on its other sides to allow a test strip to be pushed therethrough. It will similarly be apparent to one of skill in the art that such a seal cannot provide a barrier to moisture.

As will be apparent to those of skill in the art, the efficiency of a seal between two surfaces touching each other depends on the surface materials and the pressure exerted by one surface to the other or, in other words, the normal or perpendicular forces holding the surfaces together.

With respect to the first area which fails to provide a moisture free seal, the seal between the slide bar surface and the mating surface of the opening through which it extends is not efficient because attempts to form a perfect seal or increase the sealing ability by making the surfaces flatter or more resilient will increase the coefficient of friction between the two surfaces, making it more difficult to slide or move the bar in relation to the body of the device, as needed to dispense a test strip. Increasing the normal force between the two surfaces to form a perfect seal or increase the sealing ability will also increase the force needed to slide the bar.

With respect to the second area which fails to provide a moisture free seal, any attempt to increase the load to hold the two surfaces together in order to increase the seal efficiency would require an increase in the load on the end of the test strip being dispensed to push the gasket out of the way as the strip exits. This load could buckle or damage the test strip and would also increase the load on the slide bar by the user.

As such, there is continued interest in the development of new devices and methods for use in test strip dispensing. Of particular interest would be the development of such devices and methods which are easy and inexpensive to manufacture, easy to use, particularly for visually and dextrally impaired individuals, are portable and which prevent damage to the test strips from light, humidity, and other environmental contaminants including oils and the like from a user's hands.

SUMMARY OF THE INVENTION

Devices for dispensing test strips and methods of using the same are provided. The subject devices are characterized by having a housing made of a cover and a base configured to retain a plurality of test strips. In certain embodiments, the height of the base is less than the height of each of the test strips, such that a portion of each of the test strips extends beyond the distal or top edge of the base. The subject devices may further be characterized as having a substantially air and moisture tight seal. In using the subject devices, a plurality of test strips stored in a subject device are provided. A single test strip is removed from the subject device by moving the test strip distal to the remaining test strips. Also provided by the subject invention are kits for use in practicing the subject methods.

BRIEF DESCRIPTION OF THE DRAWINGS

FIG. 6 is another exemplary embodiment of a subject base assembly including a test strip engagement element having a lip extension and FIG. 6A is an exemplary embodiment showing removal of a test strip using a test strip engagement element having a lip extension. FIG. 6B shows an exemplary embodiment of a subject test strip engagement element having a data storage element.

FIGS. 7 and 7A show another exemplary embodiment of the subject invention having a slideably associated test strip engagement element and FIG. 7B shows the test strip engagement element of FIGS. 7 and 7A in association with a test strip stack.

DETAILED DESCRIPTION OF THE INVENTION

Figure 1:
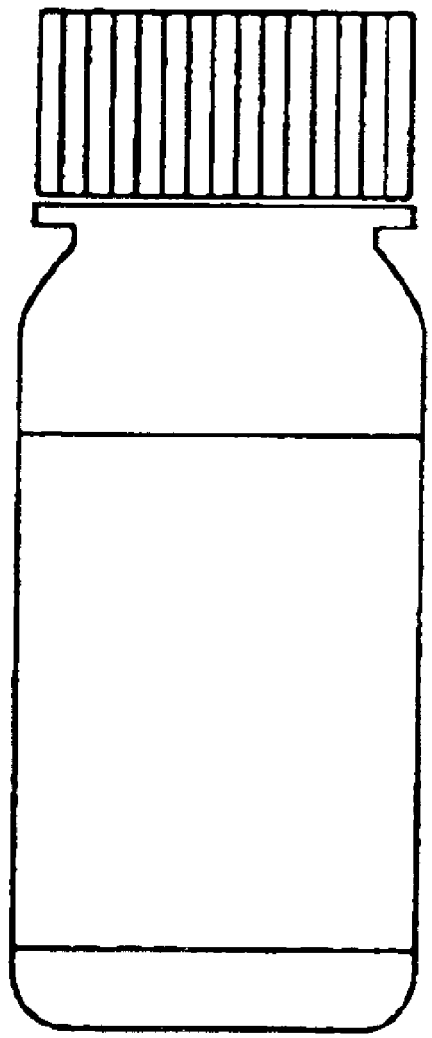
FIG. 1 is an exemplary embodiment of a conventional test strip vessel.

Devices for dispensing test strips and methods of using the same are provided. The subject devices are characterized by having a housing made of a cover and a base configured to retain a plurality of test strips. In certain embodiments, the height of the base is less than the height of each of the test strips, such that a portion of each of the test strips extends beyond the distal or top edge of the base. The subject devices may further be characterized as having a substantially air and moisture tight seal. In using the subject devices, a plurality of test strips stored in a subject device are provided. A single test strip is removed from the subject device by moving the test strip distal to the remaining test strips. Also provided by the subject invention are kits for use in practicing the subject methods.

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a reagent" includes a plurality of such reagents and reference to "the device" includes reference to one or more devices and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Devices

As summarized above, devices are provided for dispensing test strips. Particularly, devices are provided for easily dispensing a single test strip from a plurality of test strips, i.e., dispensing each test strip separately or one test strip at a time. The invention is suitable for dispensing any type of test strip for example electrochemical and colorimetric or photometric type test strips as are known in the art, where such test strips find use in the determination of a wide variety of different analyte concentrations, where representative analytes include, but are not limited to, glucose, cholesterol, lactate, alcohol, and the like. In many embodiments, the subject test strips are used to determine the glucose concentration in a physiological sample, e.g., interstitial fluid, blood, blood fractions, constituents thereof, and the like. In further describing the subject invention, a review of colorimetric and electrochemical test strips is described first to provide a proper foundation for the subject invention, where such a review is by way of example and not limitation. In other words, it will be apparent that a wide variety of test strips, including, but not limited to, colorimetric and electrochemical test strips, may be suitable for use with the present invention. The review of suitable test strips is followed by a description of the subject test strip dispenser devices.

Representative Colorimetric Test Strips

Figure 2A:
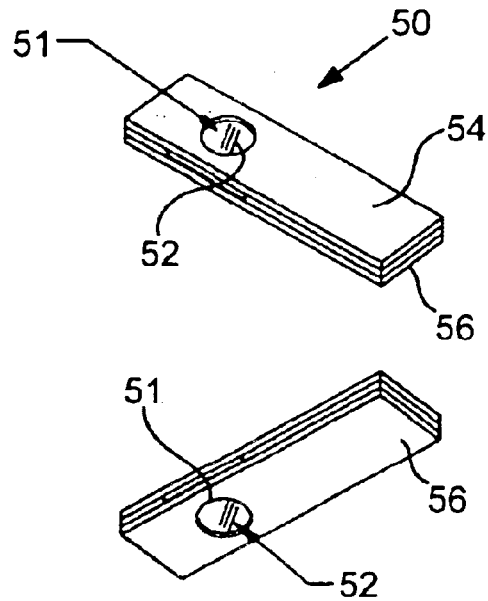
FIG. 2A is an exemplary embodiment of a colorimetric test strip suitable for use with the subject invention and FIG. 2B is an exemplary embodiment of an electrochemical test strip suitable for use with the subject invention.

The colorimetric or photometric (herein used interchangeably) reagent test strips employed in these embodiments of the subject invention are generally made up of at least the following components: a matrix for receiving a sample, a reagent composition that typically includes one or more members of an analyte oxidation signal producing system and a support element. The colorimetric test strips are typically configured and adapted to be received in an automated meter, as described below, for automatically determining the concentration of an analyte. An exemplary embodiment of a representative colorimetric test strip is shown in FIG. 2A.

The matrix 51 that is employed in the subject test strips is an inert matrix which provides a support for the various members of the signal producing system, described infra, as well as the light absorbing or chromogenic product produced by the signal producing system, i.e., the indicator. The matrix 51 is configured to provide a location for the physiological sample, e.g., blood, application and a location for the detection of the light-absorbing product produced by the indicator of the signal producing system. As such, the matrix 51 is one that is permissive of aqueous fluid flow through it and provides sufficient void space for the chemical reactions of the signal producing system to take place. A number of different matrices have been developed for use in various analyte detection assays, which matrices may differ in terms of materials, dimensions and the like, where representative matrices include, but are not limited to, those described in U.S. Pat. Nos. 4,734,360; 4,900,666; 4,935,346; 5,059,394; 5,304,468; 5,306,623; 5,418,142; 5,426,032; 5,515,170; 5,526,120; 5,563,042; 5,620,863; 5,753,429; 5,573,452; 5,780,304; 5,789,255; 5,843,691; 5,846,486; 5,968,836 and 5,972,294; the disclosures of which are herein incorporated by reference. In principle, the nature of the matrix 51 is not critical to the subject test strips and therefore is chosen with respect to other factors, including the nature of the instrument which is used to read the test strip, convenience and the like. As such, the dimensions and porosity of the test strip 50 may vary greatly, where the matrix 51 may or may not have pores and/or a porosity gradient, e.g. with larger pores near or at the sample application region and smaller pores at the detection region. Materials from which the matrix 51 may be fabricated vary, and include polymers, e.g. polysulfone, polyamides, cellulose or absorbent paper, and the like, where the material may or may not be functionalized to provide for covalent or non-covalent attachment of the various members of the signal producing system.

In addition to the matrix 51, the subject test strips further include one or more members of a signal producing system 52 which produces a detectable product in response to the presence of analyte, which detectable product can be used to derive the amount of analyte present in the assayed sample. In the subject test strips, the one or more members of the signal producing system 52 are associated, e.g., covalently or non-covalently attached to, at least a portion of (i.e., the detection region) the matrix, and in many embodiments to substantially all of the matrix.

In certain embodiments, e.g. where glucose is the analyte of interest, the signal producing system is an analyte oxidation signal producing system. By analyte oxidation signal producing system is meant that in generating the detectable signal from which the analyte concentration in the sample is derived, the analyte is oxidized by one or more suitable enzymes to produce an oxidized form of the analyte and a corresponding or proportional amount of hydrogen peroxide. The hydrogen peroxide is then employed, in turn, to generate the detectable product from one or more indicator compounds, where the amount of detectable product generated by the signal measuring system, i.e. the signal, is then related to the amount of analyte in the initial sample. As such, the analyte oxidation signal producing systems present in the subject test strips are also correctly characterized as hydrogen peroxide based signal producing systems.

As indicated above, the hydrogen peroxide based signal producing systems include an enzyme that oxidizes the analyte and produces a corresponding amount of hydrogen peroxide, whereby corresponding amount is meant that the amount of hydrogen peroxide that is produced is proportional to the amount of analyte present in the sample. The specific nature of this first enzyme necessarily depends on the nature of the analyte being assayed but is generally an oxidase. As such, the first enzyme may be: glucose oxidase (where the analyte is glucose); cholesterol oxidase (where the analyte is cholesterol); alcohol oxidase (where the analyte is alcohol); lactate oxidase (where the analyte is lactate) and the like. Other oxidizing enzymes for use with these and other analytes of interest are known to those of skill in the art and may also be employed. In those preferred embodiments where the reagent test strip is designed for the detection of glucose concentration, the first enzyme is glucose oxidase. The glucose oxidase may be obtained from any convenient source, e.g. a naturally occurring source such as *Aspergillus niger* or Penicillum, or recombinantly produced.

A second enzyme of the signal producing system may be an enzyme that catalyzes the conversion of one or more indicator compounds into a detectable product in the presence of hydrogen peroxide, where the amount of detectable product that is produced by this reaction is proportional to the amount of hydrogen peroxide that is present. This second enzyme is generally a peroxidase, where suitable peroxidases include: horseradish peroxidase (HRP), soy peroxidase, recombinantly produced peroxidase and synthetic analogs having peroxidative activity and the like. See e.g., Y. Ci, F. Wang; Analytica Chimica Acta, 233 (1990), 299–302.

The indicator compound or compounds, e.g., substrates, are ones that are either formed or decomposed by the hydrogen peroxide in the presence of the peroxidase to produce an indicator dye that absorbs light in a predetermined wavelength range. Preferably the indicator dye absorbs strongly at a wavelength different from that at which the sample or the testing reagent absorbs strongly. The oxidized form of the indicator may be a colored, faintly-colored, or colorless final product that evidences a change in color of the testing side of the membrane. That is to say, the testing reagent can indicate the presence of glucose in a sample by a colored area being bleached or, alternatively, by a colorless area developing color.

Indicator compounds that are useful in the present invention include both one- and two-component chromogenic substrates. One-component systems include aromatic amines, aromatic alcohols, azines, and benzidines, such as tetramethyl benzidine-HCl. Suitable two-component systems include those in which one component is MBTH, an MBTH derivative (see for example those disclosed in U.S. patent application Ser. No. 08/302,575, incorporated herein by reference), or 4-aminoantipyrine and the other component is an aromatic amine, aromatic alcohol, conjugated amine, conjugated alcohol or aromatic or aliphatic aldehyde. Exemplary two-component systems are 3-methyl-2-benzothiazolinone hydrazone hydrochloride (MBTH) combined with 3-dimethylaminobenzoic acid (DMAB); MBTH combined with 3,5-dichloro-2-hydroxybenzene-sulfonic acid (DCHBS); and 3-methyl-2-benzothiazolinonehydrazone N-sulfonyl benzenesulfonate monosodium (MBTHSB) combined with 8-anilino-1 naphthalene sulfonic acid ammonium (ANS). In certain embodiments, the dye couple MBTHSB-ANS is preferred.

In yet other embodiments, signal producing systems that produce a fluorescent detectable product (or detectable non-fluorescent substance, e.g. in a fluorescent background) may be employed, such as those described in: Kiyoshi Zaitsu, Yosuke Ohkura: New fluorogenic substrates for Horseradish Peroxidase: rapid and sensitive assay for hydrogen peroxide and the Peroxidase. Analytical Biochemistry (1980) 109, 109–113.

The matrix 51 is usually attached to at least one support element, herein shown as attached to two support elements 54 and 56. The support elements 54 and 56 may be of a material that is sufficiently rigid to be inserted into the meter without undue bending or kinking. In many embodiments, the support members 54 and 56 are made of material such as polyolefins, e.g., polyethylene or polypropylene, polystyrene or polyesters, where the materials support members 54 and 56 may be the same or different. Consequently, the length of at least one of the support elements typically dictates or corresponds to the length of the test strip 50.

Regardless of whether or not the length of the support elements 54 and 56 dictates or corresponds to the length of the test strip 50, the length of the test strip 50 generally ranges from about 3 mm to about 1000 mm, usually from about 10 mm to about 100 mm and more usually from about 20 mm to about 60 mm.

As described above, the support elements 54 and 56 usually are configured to enable the test strip 50 to be inserted into a meter. As such, the support elements 54 and 56, and thus the test strip 50, are typically in the form of a substantially rectangular or square-like strip, where the dimensions of the support element vary according to a variety of factors, as will be apparent to those of skill in the art, and may be the same or different.

Generally, for colorimetric assays, the sample is allowed to react with the members of the signal producing system to produce a detectable product that is present in an amount proportional to the initial amount present in the sample. The amount of detectable product, i.e., signal produced by the signal producing system, is then determined and related to the amount of analyte in the initial sample. In certain embodiments, automated meters that perform the above mentioned detection and relation steps are employed. The above described reaction, detection and relating steps, as well as instruments for performing the same, are further described in U.S. Pat. Nos. 4,734,360; 4,900,666; 4,935,346; 5,059,394; 5,304,468; 5,306,623; 5,418,142; 5,426,032; 5,515,170; 5,526,120; 5,563,042; 5,620,863; 5,753,429; 5,573,452; 5,780,304; 5,789,255; 5,843,691; 5,846,486; 5,968,836 and 5,972,294; the disclosures of which are herein incorporated by reference.

Examples of such colorimetric reagent test strips suitable for use with the subject invention include, but are not limited to, those described in U.S. Pat. Nos. 5,563,042; 5,753,452; 5,789,255, herein incorporated by reference.

Representative Electrochemical Test Strips

Figure 2B:
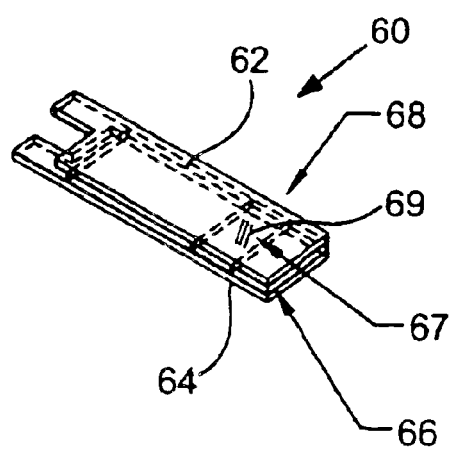

Generally, the electrochemical test strips used with the subject invention are made up of two opposing metal electrodes separated by a thin spacer layer, where these components define a reaction area or zone. In many embodiments a redox reagent system is located in the reaction area or zone. The electrochemical test strips are usually configured and adapted to be received in an automated meter, as described below, for automatically determining the concentration of an analyte. An exemplary embodiment of a representative electrochemical test strip 60 is shown in FIG. 2B.

In certain embodiments of these electrochemical test strips, the working and reference electrodes 62 and 64 are generally configured in the form of elongated rectangular strips. Typically, the length of the electrodes 62 and 64 ranges from about 1.9 cm to about 4.5 cm, usually from about 2.0 cm to about 2.8 cm. The width of the electrodes 62 and 64 ranges from about 0.07 cm to about 0.76 cm, usually from about 0.24 cm to about 0.60 cm. The working and reference electrodes 62 and 64 each have a thickness typically ranging from about 10 mm to about 100 nm and usually from about 10 mm to about 20 nm.

The working and reference electrodes 62 and 64 are further characterized in that at least the surfaces of the electrodes that face the reaction area 67 of the electrochemical cell in the strip is a metal, where metals of interest include palladium, gold, platinum, silver, iridium, carbon (conductive carbon ink), doped tin oxide, stainless steel and the like. In many embodiments, the metal is gold or palladium.

While in principle the entire electrode may be made of the metal, each of the electrodes is generally made up of an inert support material on the surface of which is present a thin layer of the metal component of the electrode. In these more common embodiments, the thickness of the inert backing material typically ranges from about 25 to 500 $\mu$m, usually from about 50 to 400 $\mu$m, while the thickness of the metal layer typically ranges from about 10 to 100 nm and usually from about 10 to 40 nm, e.g., a sputtered metal layer. Any convenient inert backing material may be employed in the subject electrodes, where typically the material is a rigid material that is capable of providing structural support to the electrode and, in turn, the electrochemical test strip as a whole. Suitable materials that may be employed as the inert support material include plastics, e.g., polyethylene terephthalate (PET), polyethylene terephthalate, glycol modified (PETG), polyimide, polycarbonate, polystyrene, silicon, ceramic, glass, and the like.

The working and reference electrodes 62 and 64 as described above generally face each other and are separated by only a short distance, such that the distance between the working and reference electrodes in the reaction zone or area 67 of the electrochemical test strip is extremely small. This minimal spacing of the working and reference electrodes 62 and 64 in the electrochemical test strips is a result of the presence of a thin spacer layer 66 positioned or sandwiched between the working and reference electrodes. The thickness of this spacer layer 66 may range from about 50 to 750 $\mu$m, and usually ranges from about 100 to 175 $\mu$m. The spacer layer 66 is cut so as to provide a reaction zone or area 67, where in many embodiments the volume of the reaction area or zone 67 typically ranges from about 0.1 to 10 $\mu$L, usually from about 0.2 to 5.0 $\mu$L. The spacer layer may have a circular reaction area cut with side inlet and outlet vents or ports, or other configurations, e.g., square, triangular, rectangular, irregularly shaped reaction areas, etc. The spacer layer 66 may be fabricated from any convenient material, where representative suitable materials include polyethylene terephthalate (PET), polyethylene terephthalate, glycol modified (PETG), polyimide, polycarbonate, and the like, where the surfaces of the spacer layer 66 may be treated so as to be adhesive with respect to their respective electrodes and thereby maintain the structure of the electrochemical test strip 60.

In many embodiments, a reagent system or composition 69 is present in the reaction area, where the reagent system 69 interacts with components in the fluid sample during the assay. Reagent systems of interest typically include a redox couple.

The redox couple of the reagent composition, when present, is made up of one or more redox couple agents. A variety of different redox couple agents are known in the art and include: ferricyanide, phenazine ethosulphate, phenazine methosulfate, pheylenediamine, 1-methoxy-phenazine methosulfate, 2,6-dimethyl-1,4-benzoquinone, 2,5-dichloro-1,4-benzoquinone, ferrocene derivatives, osmium bipyridyl complexes, ruthenium complexes, and the like. In many embodiments, redox couples of particular interest are ferricyanide, and the like.

Other reagents that may be present in the reaction area include buffering agents, e.g., citraconate, citrate, malic, maleic, phosphate, "Good" buffers and the like. Yet other agents that may be present include: divalent cations such as calcium chloride, and magnesium chloride; surfactants such as Triton, Macol, Tetronic, Silwet, Zonyl, and Pluronic; stabilizing agents such as albumin, sucrose, trehalose, mannitol, and lactose.

Examples of such a reagent test strips suitable for use with the subject invention include those described in copending U.S. application Ser. Nos. 09/333,793; 09/497,304; 09/497,269; 09/736,788 and 09/746,116, the disclosures of which are herein incorporated by reference.

Generally for electrochemical assays, an electrochemical measurement is made using the reference and working electrodes. The electrochemical measurement that is made may vary depending on the particular nature of the assay and the device with which the electrochemical test strip is employed, e.g., depending on whether the assay is coulometric, amperometric or potentiometric. Generally, the electrochemical measurement will measure charge (coulometric), current (amperometric) or potential (potentiometric), usually over a given period of time following sample introduction into the reaction area. Methods for making the above described electrochemical measurement are further described in U.S. Pat. Nos. 4,224,125; 4,545,382; and 5,266,179; as well as WO 97/18465; WO 99/49307; the disclosures of the priority documents of which are herein incorporated by reference. Regardless of the type of measurement, an electrochemical measurement or signal is made in the reaction zone of the test strip.

Following detection of the electrochemical measurement or signal generated in the reaction zone as described above, the amount of the analyte present in the sample introduced into the reaction zone is then determined by relating the electrochemical signal to the amount of analyte in the sample. A representative reading device for automatically practicing these steps, such that user need only apply sample to the reaction zone and then read the final analyte concentration result from the device, is further described in copending U.S. application Ser. No. 09/333,793 filed Jun. 15, 1999, the disclosure of which is herein incorporated by reference.

Test Strip Dispensers

As described above, the subject invention includes devices for dispensing a single test strip for use from a plurality of stored test strips, where the subject devices protect the retained test strips from adverse contaminants and conditions such as light, humidty, dust, dirt and oils or other contaminants from human hands, etc. Typically, the subject devices are configured to retain from about 5 to about 100 test strips at one time, usually about 10 to about 80 test strips at one time and more usually from about 20 to about 60 test strips at one time, however the subject devices may be configured to retain more or fewer test strips. The subject devices also allow for easy re-loading of additional test strips, as will be apparent from the descriptions below.

Accordingly, the subject devices include a two piece housing, where such a housing is made up of two separate and separable assemblies: a cover assembly and a base assembly. In other words, the cover and base are not attached together. Such a separable configuration advantageously enables substantially air and moisture tight seals to be created and maintained between the cover and base by a variety of means, as will be described in more detail below. The size and shape of the housing will necessarily vary depending on a variety of factors, where such factors include, but are not limited to, the type and number of test strips retained therein, and the like. Accordingly, the shape of the housing may take any of a variety of shapes ranging from simple to complex. For example, the housing may be of a substantially rectangular, substantially square, substantially cylindrical, substantially round, substantially circular, substantially elliptical or substantially oval shape, etc., where in certain embodiments, circular, round or cylindrical or substantially circular, substantially round or substantially cylindrical shapes are of particular interest such that they enable a threaded engagement between the cover and base assemblies. In other words, in many embodiments, the device is shaped to enable a threadable engagement between the cover and base assemblies. Alternatively, as mentioned, the shape may be more complex such as a substantially irregular shape or the like.

Likewise, the size of the housing may also vary depending on a variety of factors such as the type and number of test strips retained therein, and the like. In certain embodiments, the housing is configured such that the plurality of test strips is retained in the base portion of the housing. However, as will be apparent, in certain embodiments of the subject devices the test strips may be retained in the cover instead. In many of these embodiments of the subject devices, the height of the base assembly is less than the length of each of the test strips retained therein, i.e., a portion of each of the retained test strips extends beyond the distal edge or top portion of the base assembly, where usually the portion of the test strip that extends beyond the base assembly is the contact or non-testing area of the test strip so as to enable an individual to easily grasp a single test strip while avoiding many of the problems associated with prior art devices. For example, the height of the base assembly is typically at least about two thirds the length of each test strip (i.e., about one third of each test strip protrudes above the distal edge of the base assembly), where the height of the base assembly may be as little as about one half or one quarter or less the length of each test strip. By way of example and not limitation, for those embodiments having a substantially cylindrical shape and configured to retain from about 10 to 60 test strips, each having a length ranging from about 20 mm to about 60 mm, the total height of the housing (i.e., the base and cover assemblies together) will typically range from about 20 mm to about 1300 mm, usually from about 25 mm to about 110 mm and more usually from about 25 mm to about 65 mm and the width or diameter of the housing will typically range from about 10 mm to about 40 mm, usually from about 10 mm to about 30 mm and more usually from about 15 mm to about 20 mm. As such, the height of the base assembly will typically range from about 5 mm to about 700 mm, usually from about 10 mm to about 40 mm and more usually from about 15 mm to about 30 mm and the height of the cover assembly will typically range from about 4 mm to about 600 mm, usually from about 8 mm to about 35 mm and more usually from about 15 mm to about 25 mm.

The housing may be manufactured from a variety of materials, where the bottom and cover of the housing may be manufactured from the same or different materials, but where such materials will not substantially interfere with the testing reagents of the test strips retained therein. Examples of such materials may include, but are not limited to, plastics such as polytetrafluoroethylene, polypropylene, polyethylene, polystyrene, polycarbonate and blends thereof, metals such as stainless steel, aluminum and alloys thereof, siliceous material, e.g., glass materials, and the like.

The cover and base assemblies are alignable in a closed configuration such that the housing is substantially air and moisture tight when in a closed configuration, i.e., the cover will form a substantially air and moisture tight seal with the base when the two are contacted together in a closed position. By substantially air and moisture tight seal is meant that the housing is capable of preventing substantial air and moisture from entering the housing when the housing is in a closed position. In other words, when in a mated configuration, the inside of the housing is a substantially air tight and moisture free environment and more specifically the test strips inside the housing are in a substantially air tight and moisture free environment when the housing is in a closed configuration.

In order to accomplish the above described substantially air and moisture free environment, the housing includes at least one attachment means, where such attachment means aligns and mates, i.e., attaches, the base and cover assemblies together to form an intimate seal, i.e. a seal that is substantially air and moisture tight. Representative attachment means include, but are not limited to, at least one of: one or more threaded engagements, i.e., one or more thread locking means, a snap fit mechanism, a frictional engagement, a cover seating mechanism, an O-ring gasket, a lock and key mechanism and a tensioning clamp, where each of these will now be describe in more detail.

As mentioned above, a threaded engagement, i.e., one or more thread locking means may be employed to form an intimate contact between the base and cover assemblies. For example, the cover assembly may include one or more threads such as a ¼, ½, ¾ or more thread(s) on the inside of the cover assembly, where such a thread(s) corresponds and operatively associates with a similar thread(s) positioned on the base assembly. As such, when mated together, for example with a ¼, ½, ¾ or greater turn (i.e., a torque is applied by threadably engaging the corresponding threads) to engage the threads, the thread(s) of the base and cover are configured to align and clamp the two assemblies together to form an intimate seal between the cover and the base, i.e., a substantially air and moisture proof seal. It will be appreciated that the shape of the device will advantageously allow for such threaded engagement. In other words, the ability to position the seal in a substantially circular, conical, etc., area enables use of the corresponding helical threads.

A frictional engagement, i.e., a seating mechanism, may be employed to form an intimate contact between the base and cover assemblies. In this particular embodiment, pressure between the surfaces of the base and cover assemblies is maximized by mating two surfaces together with force. For example, the cover assembly may include one or more protrusions or sealing surfaces inside the cover which mates or seats adjacent a sealing surface or edge or ledge of the base assembly and/or the assemblies may be dimensioned such that a frictional force is applied upon insertion of the cover assembly over the base assembly, or vice versa. As such, when seated, the base and cover are forced together to create an intimate seal, i.e., a substantially air and moisture proof seal.

Furthermore, an O-ring gasket may be employed to form an intimate contact between the base and cover assemblies. For example, an O-ring may be positioned on the cover or the base to form an intimate contact when the cover and base are in a closed position.

Still further, a lock and key mechanism may be employed. For example, the cover may include a protrusion on its inside which mates with a corresponding groove on the base, or vice versa, to secure the assemblies in an intimately contacted configuration.

Yet further, a tensioning clamp similar to that which is used to fasten and close ski boots (see for example U.S. Pat. No. 6,145,168, the disclosure of which is herein incorporated by reference) may be employed. As such, a gripping arm or the like may be coupled to the outside of the cap. For example, once the cover is brought into a closing configuration with the base, such a gripping arm interacts with one of a plurality of teeth which protrude from the outside of the base. The two are further associated by moving an actuating arm associated with the gripping arm to apply a force or tension to the clamp, thus moving the cap and base closer together to form a secure seal.

A snap fit mechanism may be employed. By snap fit mechanism is meant any suitable "built in" or integral latching mechanism for attaching one part to another. A snap fit is different from loose or chemical attachment methods in that it requires no additional pieces, materials or tools to carry out the attaching function. Representative snap fit mechanisms suitable for use with the present invention are described in Bonenberger, P., The First Snap-Fit Handbook, Hanzer (2000), incorporated herein in its entirety, and include, but are not limited to, planar snap fit, cantilever snap fit, trap snap fit, torsion snap fit and annular snap fit.

As noted above, one or more, sometimes two or three or more of the above described attachment means may be used to create an intimate seal between the cover and the base, where such a closure enables a substantially air and moisture tight seal.

The subject device may further include moisture absorbent reagents or components such as desiccant material, silica gel and the like, where such material is capable of absorbing moisture from the environment surrounding the stored test strips. Such absorbent reagents or components may be retained in one or more compartments positioned inside the cover and/or base assemblies.

In order to effect and maintain the substantially air and moisture tight seal, the cover (or optionally the base) may include a sealing ridge configured such that a corresponding groove of the base (or the cover if the ridge is positioned on the base) is configured to receive and mate with the ridge of the cover when the cover and the base are in a closed position. The ridge is typically tapered to enable the edges of the base (or the cover if the ridge is positioned on the base) to fit snuggly between the ridge and the walls of the cover. Accordingly, a sealing ridge is positioned on a first assembly such as a cover and the second assembly such as a base, in this particular example, includes a corresponding groove configured to accept the ridge of the first assembly such that the ridge is snuggly fit in the groove of the second assembly to provide a substantially air and moisture tight seal.

The base of the present invention (or the assembly which retains the test strips) may also include an urging means, where such an urging means is capable of applying a force to the test strips stored in the device to assist in dispensing and preventing the test strips from inadvertently falling out of the housing. The urging means may be integral with the housing, i.e., a unitary piece of construction, or may be a separate piece of material or separate component. A variety of urging means may be used to accomplish such an applied force to the test strips, where representative means or mechanisms include, but are not limited to, a spring such as a coil or leaf spring, etc., a sponge, foam, and a pusher or plunger rod. In certain embodiments, the urging means may exert a force from one or more than one direction of the test strips, for example the urging means may exert a force from all directions or opposing forces from two directions, etc. For example, a force may be exerted from a first direction such that the urging means exerts a force to a test strip on one end of the test strip stack and a second force may be exerted from a second direction such that the urging means exerts a force, e.g., an opposing force, to a test strip on the opposite end of the test strip stack from the first test strip, where the first and second forces may be applied by the same or different mechanisms.

In addition to, or in place of the above described urging means, a substantially planar, rigid plate may be employed to hold the test strips together in a suitable orientation or arrangement. For example, one or more such substantially planar, rigid plates may be configured to contact one or both ends of the test strip stack to assist in dispensing the test strips and preventing the test strips from inadvertently falling out of the housing. In certain embodiments, the plate may include one or more protrusions to limit or minimize the degree of contact between the plate and an adjacent test strip such that only the protrusion(s) contact an adjacent test strip, as opposed to the all or substantially all of the planar face of the plate contacting the test strip.

In certain embodiments, the base assembly, more specifically the bottom side of the base assembly, i.e., the side against which the ends of the test strips lie, may converge to an apex, i.e., extends inward of the base, or may include a pattern or one or more protrusions thereon, to enable further segregation of the test strips retained therein. In other words, the base may include test strip segregation means, where such means enable the test strips to be stepped, staggered or otherwise segregated to facilitate the removal of a single test strip from the stack.

In certain embodiments of the subject devices, a test strip engagement element is included, where such a test strip engagement element is configured to enable removal of a single test strip from a plurality of test strips stored in the housing, i.e., from a stack of stored test strips. The test strip engagement element may be integral with the housing, i.e., may be a unitary piece of construction or may be a separate piece of material or component, where such a component may be fixed in place or may be readily removable.

As described above, the test strip engagement element facilitates removal of a single test strip from a plurality of test strips stored in the housing. Additionally, the test strip engagement element is also configured to prevent removal of any and all other test strips, i.e., it only enables one test strip to be removed at a time.

Accordingly, in certain embodiments, the test strip engagement element includes a lip extension at its distal end, where the lip extension is configured to allow a single test strip to slide or move along its surface, i.e., advance adjacent its surface, while catching any and all other test strips under the lip extension. In certain embodiments of the subject invention, the test strip engagement element is multi sided such that each side is symmetrical, i.e., substantially the same as any other side, where such a configuration enables a greater number of test strips to be dispensed. For example, the exact number of sides will vary depending on the particular configuration of the engagement element, the test strips to be dispensed, etc. For example, the engagement element may have two sides, i.e., two test strip dispensing sides, or more. That is, in those embodiments where the engagement element is double sided, lips extend over two sides of a central area such that there is a first lip extending over a first side and a second lip extending over a second side. As such, a first plurality or stack of test strips may be positioned adjacent a first side of the engagement element and a second plurality or stack may be positioned adjacent a second side of the engagement element.

In certain other embodiments of the subject test strip engagement element, the test strip engagement element includes at least one test strip grasping means, where such a test strip grasping means is configured to grasp or hold a single test strip and advance or move the grasped test strip in a direction away from the test strip stack, either automatically or manually. In other words, a test strip engagement element having at least one test strip grasping means may move a test strip automatically or manually by a finger or the like. Regardless of whether the test strip engagement element having at least one test strip grasping means is actuated automatically or manually, a variety of grasping means may be employed to grasp a test strip.

Accordingly, test strip engagement element is slideably associated with a portion of the housing such as the base assembly. The test strip engagement element includes a handle at its distal end to facilitate sliding the engagement element by an individual. The handle is attached to a connection means such as a rod or plate or the like, which is further associated with at least one grasping means such as at least one ledge, tooth or arm laterally extending from the proximal end of the engagement element. In other words, at least one ledge, tooth or arm extends from the proximal end substantially perpendicular to the connection means, e.g., a rod or plate mid portion. The grasping means is thus configured to engage an end or edge of a test strip and to move it, i.e., slideably move it or carry it forward, in a direction away from the remaining test strips, i.e., a direction distal to the stack of test strips or substantially out of the housing, so that the single test strip is easy to grasp for removal from the housing.

In other embodiments, in addition to or in place the above described ledge, tooth or arm positioned at the proximal end of the engagement element, the engagement element may include a magnet means for magnetically engaging a test strip also having a magnet means and moving the test strip. Still further, a surface or area of the engagement element may include a coating layer such as an adhesive or the like to facilitate engagement of a test strip and/or may include a pattern such as a pattern of ridges and/or protrusions to facilitate engagement of a test strip.

The test strip engagement element may be configured to include a data storage element capable of storing data pertaining to the test strips stored in the housing, such as calibration data, expiration date, the number strips used/available, and the like, where the data may be easily transferred or communicated to an external device such as a meter for automatically determining the presence or concentration of at least one analyte in the physiological sample, where such meters are known in the art. The data storage element may be in any convenient form, depending on a variety of factors such as the amount of data to be stored and the like, where representative data storage elements include, but a are not limited to, a bar code, electronic storage element, and the like. In certain embodiments, the test strip engagement element also includes electrical contacts or other suitable means for operatively coupling or transferring data to such an external device such as a meter or the like.

The base assembly may further include a test strip movement means for automatically advancing or moving a top most test strip in a direction away from the remaining test strips. In other words, the subject test strip dispensers may include a means for automatically advancing a test strip. As such, in certain embodiments of the subject devices, a test strip movement means is provided, where such a movement means may be actuated by a button or the like present on the exterior of the device. The movement means may include any suitable means capable of engaging and moving a test strip automatically.

Figure 3:
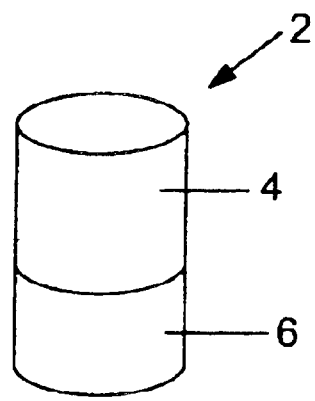
FIG. 3 is an exemplary embodiment of a subject test strip dispensing housing.

Referring now to the Figures, where like numerals represent like features or components, FIG. 3 shows an external view of an exemplary embodiment of a housing assembly 2, as described above. Accordingly the housing assembly 2 includes a base assembly 6 and a cover assembly 4, herein shown in a closed position. As described above, in such a closed position, the housing is substantially air and moisture tight. In this particular embodiment, the housing is shown having a cylindrical shape; however, as mentioned above, the housing may be of any convenient shape.

Figure 4:
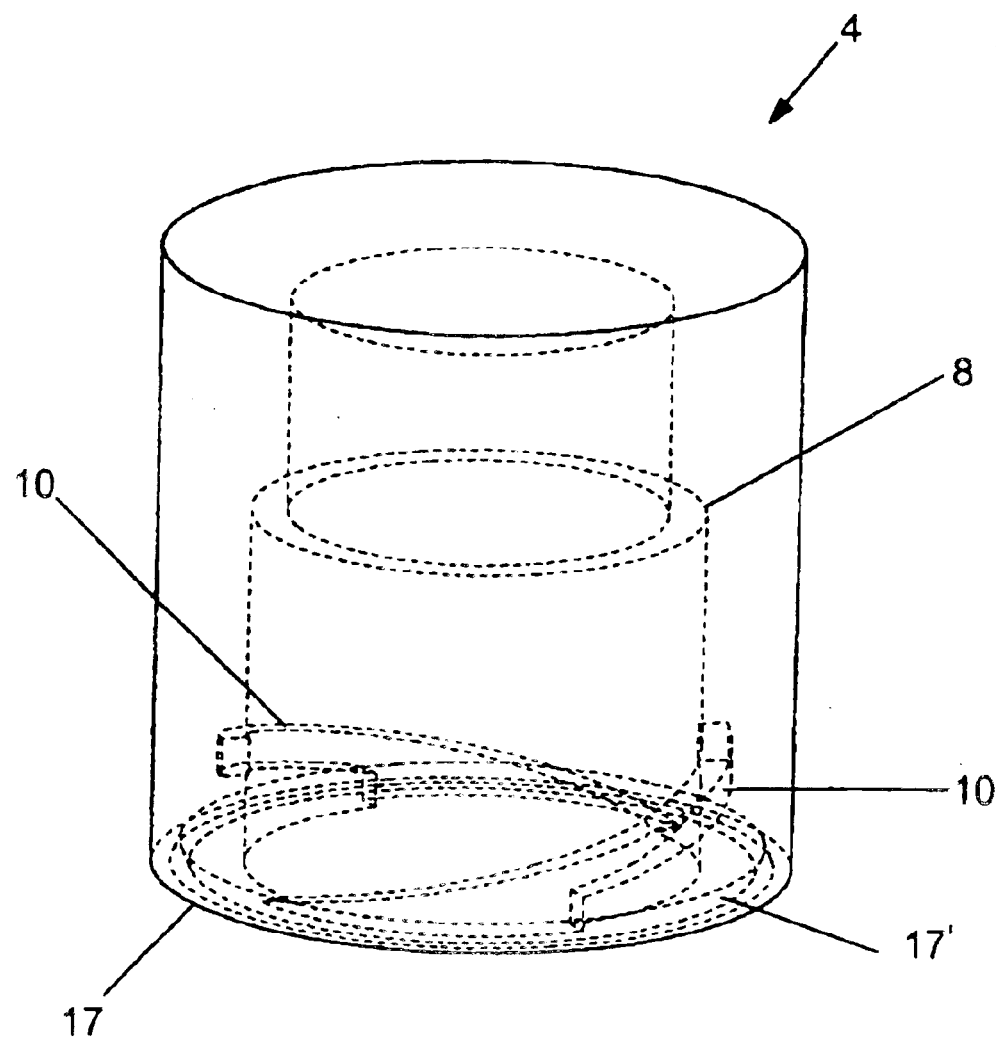
FIG. 4 is an exemplary embodiment of a subject cover assembly of a subject housing showing the internal structure in phantom.

FIG. 4 shows an exemplary embodiment of a subject cover assembly of a subject housing showing the internal structure, such as cover assembly 4 of FIG. 3. Cover assembly 4 includes three attachment means, each of which is capable of forming an intimate contact between the base and cover assemblies.

Figure 5:
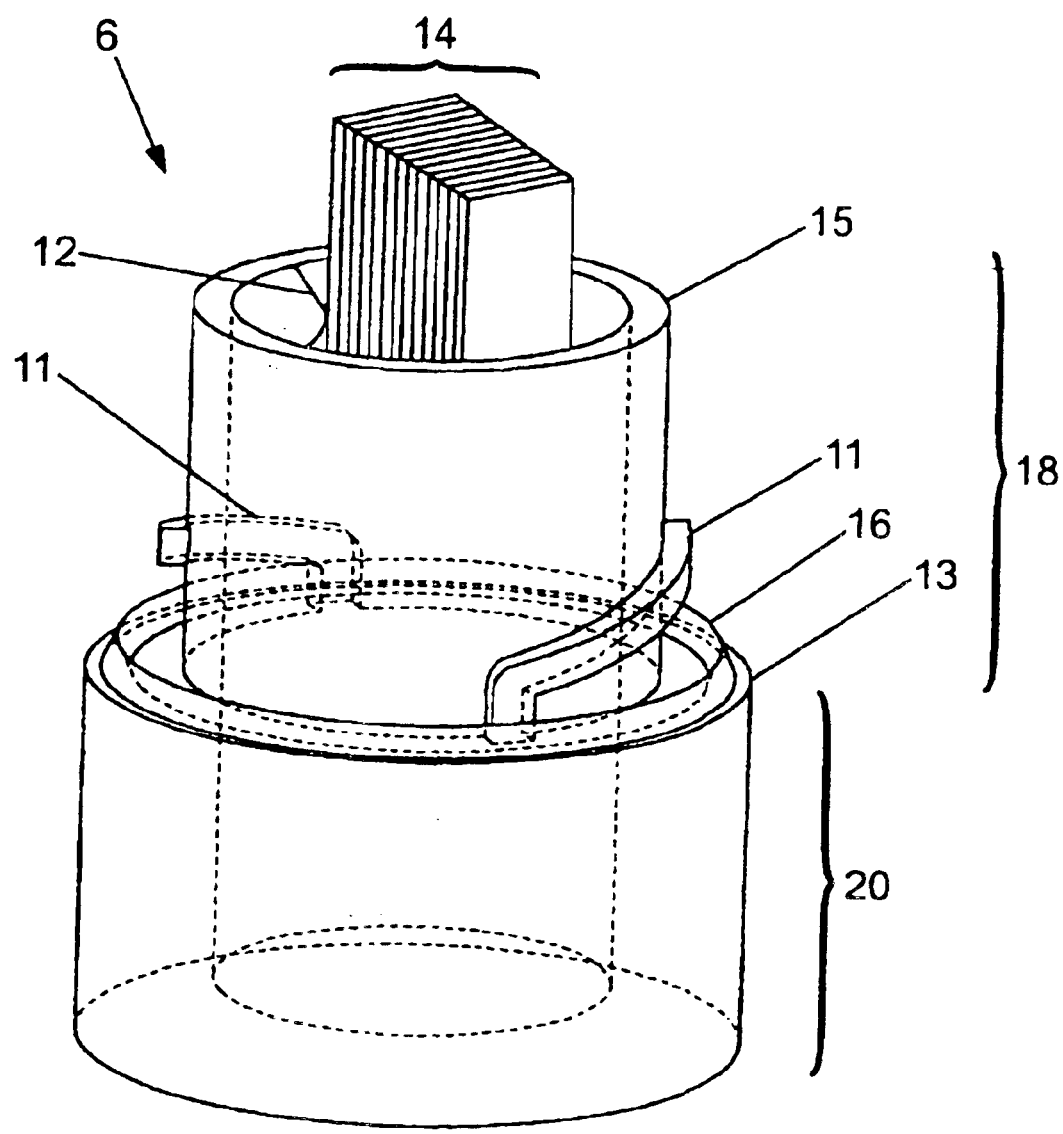
FIG. 5 is an exemplary embodiment of a subject base assembly of a subject housing.

In this particular embodiment, the seating mechanism 8 includes a protrusion or ledge 8, i.e., a sealing surface 8, positioned inside the cover assembly which frictionally mates or seats adjacent a distal edge, lip or ledge, i.e., a sealing surface, of a base assembly such as sealing surface or edge 15 of base assembly 6 of FIG. 5, herein shown as a protrusion or ledge 8 which encircles the inside perimeter of the cover; however, it will be apparent that the protrusion need not encircle the entire perimeter. As described below, in certain embodiments, the sealing surface 8 may include a sealing ridge or groove, as will be described below.

Similarly, sealing surface 17 of cover 4, i.e., edge, ledge or lip 17, also mates or seats against a sealing surface, i.e., edge, lip or ledge of a corresponding base assembly component, such as sealing surface or edge 13 of FIG. 5, for example. In certain embodiments, one or more sealing surfaces will include a sealing ridge for mating with a corresponding sealing groove on a corresponding assembly, as will be further described below. For example, a base assembly may include a sealing ridge positioned on a sealing surface (see for example ridge 16 of FIG. 5 and ridge 15' of FIG. 5A) and a corresponding cover may include a sealing groove, such as sealing groove 17' of FIGS. 4 and 4A and groove 8' of FIG. 4B, for receiving the sealing ridge when the base and cover are mated together in a closed configuration (see for example FIG. 5B which shows a base assembly having a sealing ridge positioned on a sealing surface 13 and a corresponding cover assembly having a sealing groove positioned on a sealing surface 17, wherein the two are mated to form an intimate seal or FIG. 4C which shows a cover having a sealing groove positioned on a sealing surface 8 mated with a base having a sealing ridge positioned on a sealing surface 15 to form an intimate seal). Thus, when the sealing groove and sealing ridge are mated together, the base and cover assembly are forced together to create an intimate seal, i.e., a substantially air and moisture proof seal.

Figure 4A:
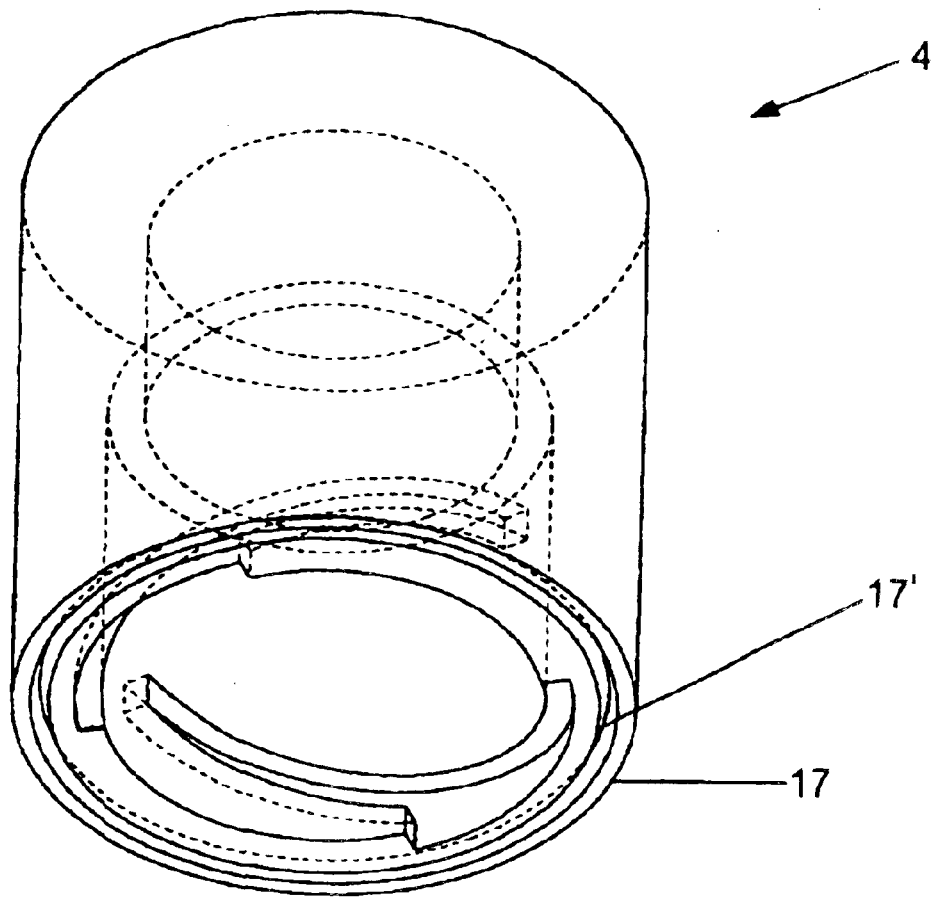
FIG. 4A is a perspective view of the cover of FIG. 4 showing the sealing groove positioned on a sealing surface.

FIG. 4A shows a perspective view of cover 4. Accordingly, the cover 4 has been rotated about 45° about an axis transverse to the longitudinal axis of the cover 4. FIG. 4A shows sealing surface 17 having sealing groove 17' described above positioned thereon for receiving a sealing ridge positioned on a base assembly such as sealing ridge 16 of FIG. 5. As noted above, the cover assembly, e.g., the sealing surface 17 may instead include a sealing ridge and a corresponding base assembly could instead include the mateable sealing groove.

Figure 4B:
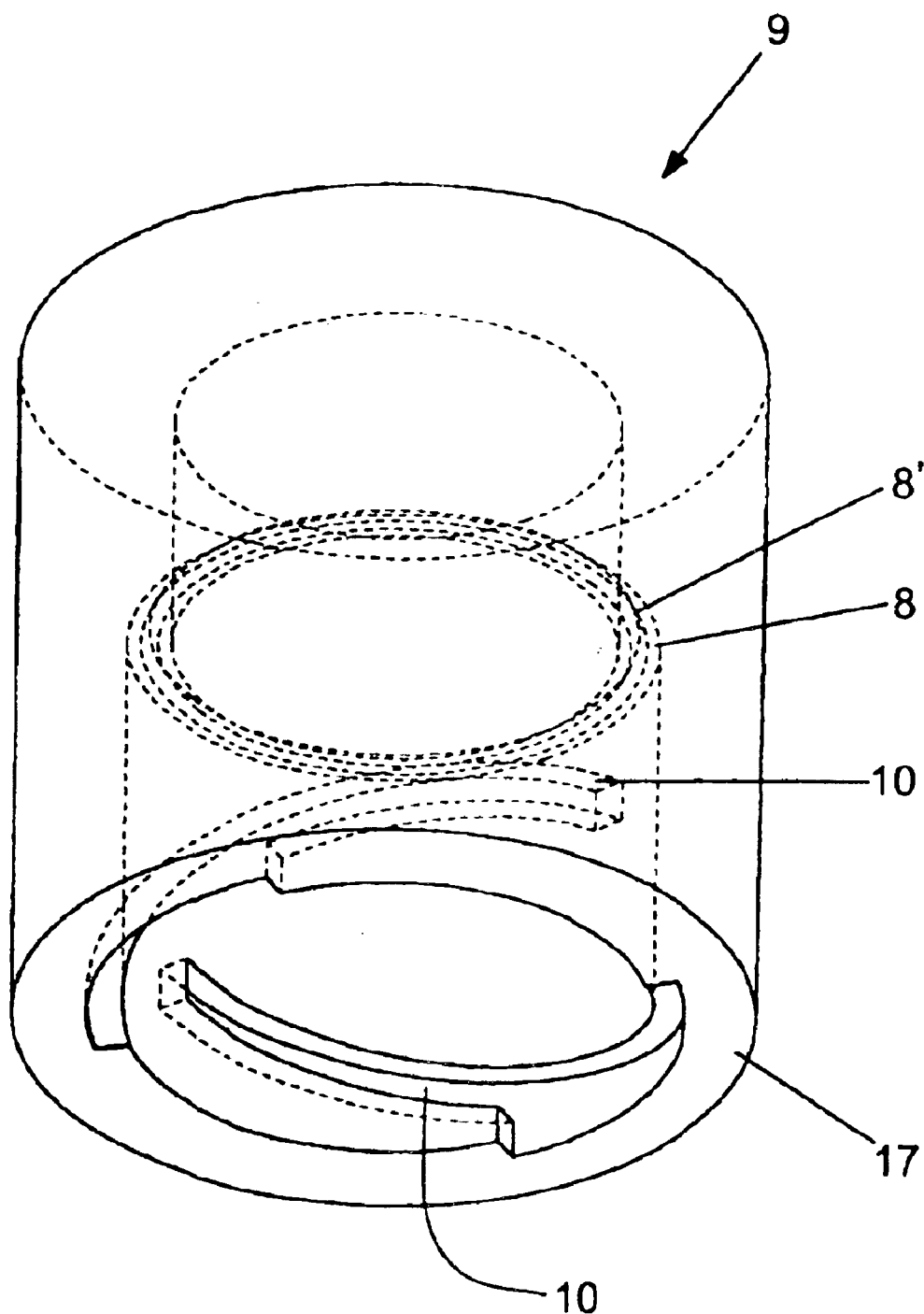
FIG. 4B is an exemplary embodiment of a cover assembly according to the subject invention having a sealing groove positioned on a sealing surface of the interior of the cover.
Figure 4C:
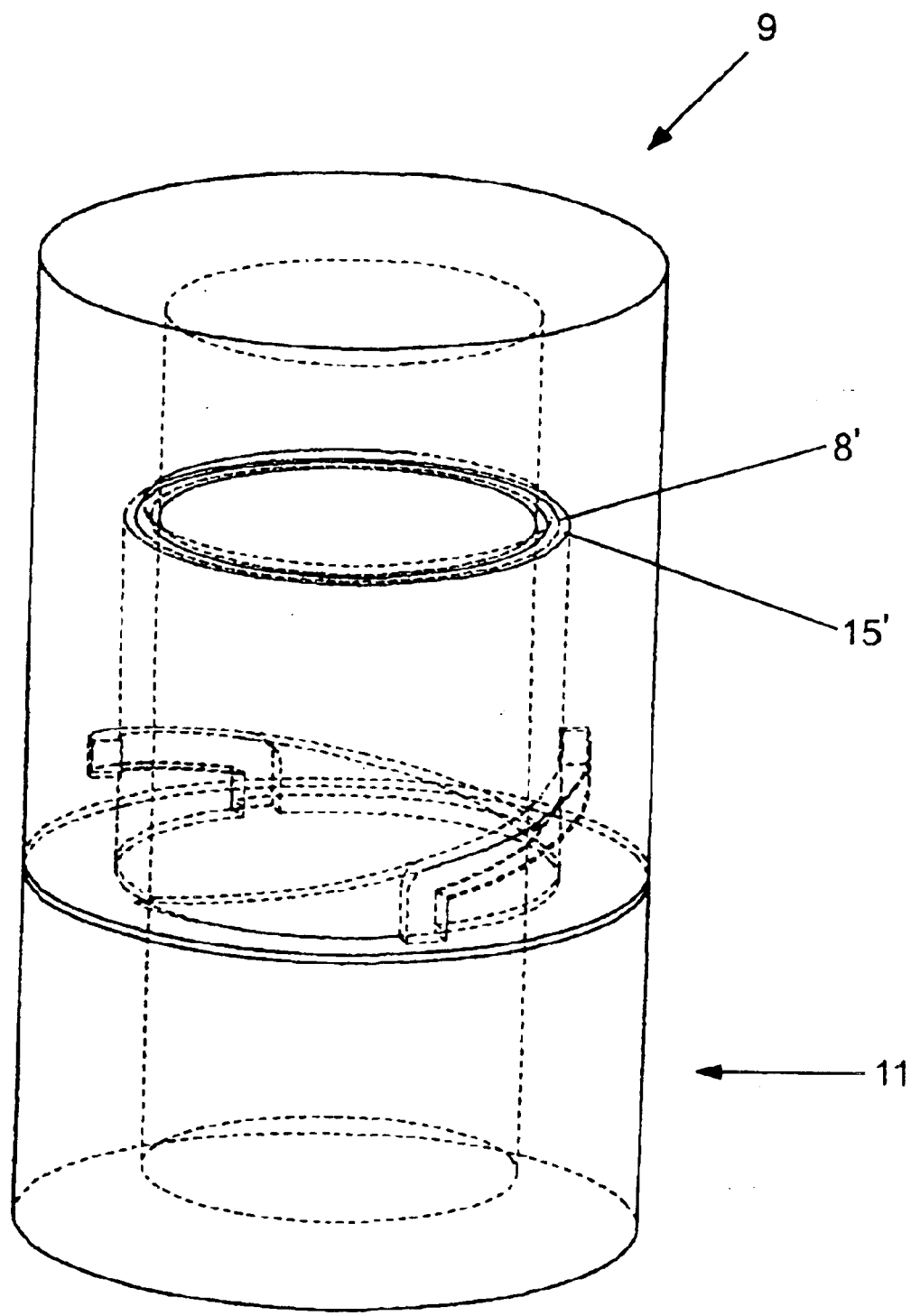
FIG. 4C shows an exemplary device according to the subject invention wherein the base and cover are mated together to form an intimate seal by way of at least corresponding threads and a sealing ridge and mated sealing groove, such as sealing ridge 15' of FIG. 5A and sealing groove 8' of FIG. 4B.

As mentioned above, a sealing ridge or sealing groove may also or alternatively be positioned on another sealing surface of the cover. FIG. 4B shows a sealing groove 8' positioned on sealing surface 8 of cover 9, which may be in addition to or in place of a groove or ridge positioned on sealing surface 17 of the cover assembly. As noted above, sealing surface 8 may instead include a sealing ridge. Sealing groove 8' is configured to mate with a corresponding sealing ridge on a base assembly, such as sealing ridge 15' positioned on a sealing surface 15 of base 11 of FIG. 5A. As described above, FIG. 4C shows a cover having a sealing groove 8' positioned on a sealing surface 8 mated with a base having a corresponding sealing ridge 15' positioned on a sealing surface 15 to form an intimate seal.

Cover assembly 4 also includes two thread locking means 10, such as two ¼ turn threads (as mentioned, a ¾ turn thread, ½ turn thread, 1 turn thread or thread having more than 1 turn may also be used, as will be obvious to one of skill in the art), as described above. As noted above, the threads advantageously allow a small hand torque to create a large or substantial sealing pressure or force on the sealing surfaces.

FIG. 5 shows a view of an exemplary base assembly, such as base assembly 6 of FIG. 3. Base assembly 6 is shown having a plurality of test strips 14 stored therein, where the test strips are urged together by urging means 12. Base assembly 6 also includes an attachment means, herein shown as thread locking means 11, e.g., ¼ turn threads (or threads having less or more turns) positioned on the exterior of the base, which corresponds to the thread locking means 10 positioned on the interior of the cover assembly 4, as described above. Base assembly 6 may be made of two or more sections, as seen here as two integral sections 18 and 20, where section 18 has a smaller diameter than section 20 so as to accommodate a cover assembly and create a flush housing exterior. At the interface of sections 18 and 20 is sealing surface 13 having a tapered or substantially "V" shaped sealing ridge 16, which is configured to be received or mated with a corresponding sealing groove positioned on a sealing surface of a cover, such as sealing groove 17' of sealing surface or edge 17 of cover 4 of FIG. 4, such that the ridge 16 is fit snuggly in the groove of a corresponding cover. Optionally, as mentioned above, it will be apparent that the base may include a sealing groove such that a sealing ridge of a cover may be fit or received by a groove of a base to provide a substantially air and moisture tight seal. As noted above, the seal surface or edge of either the base or cover may further include a gasket (not shown).

Figure 5A:
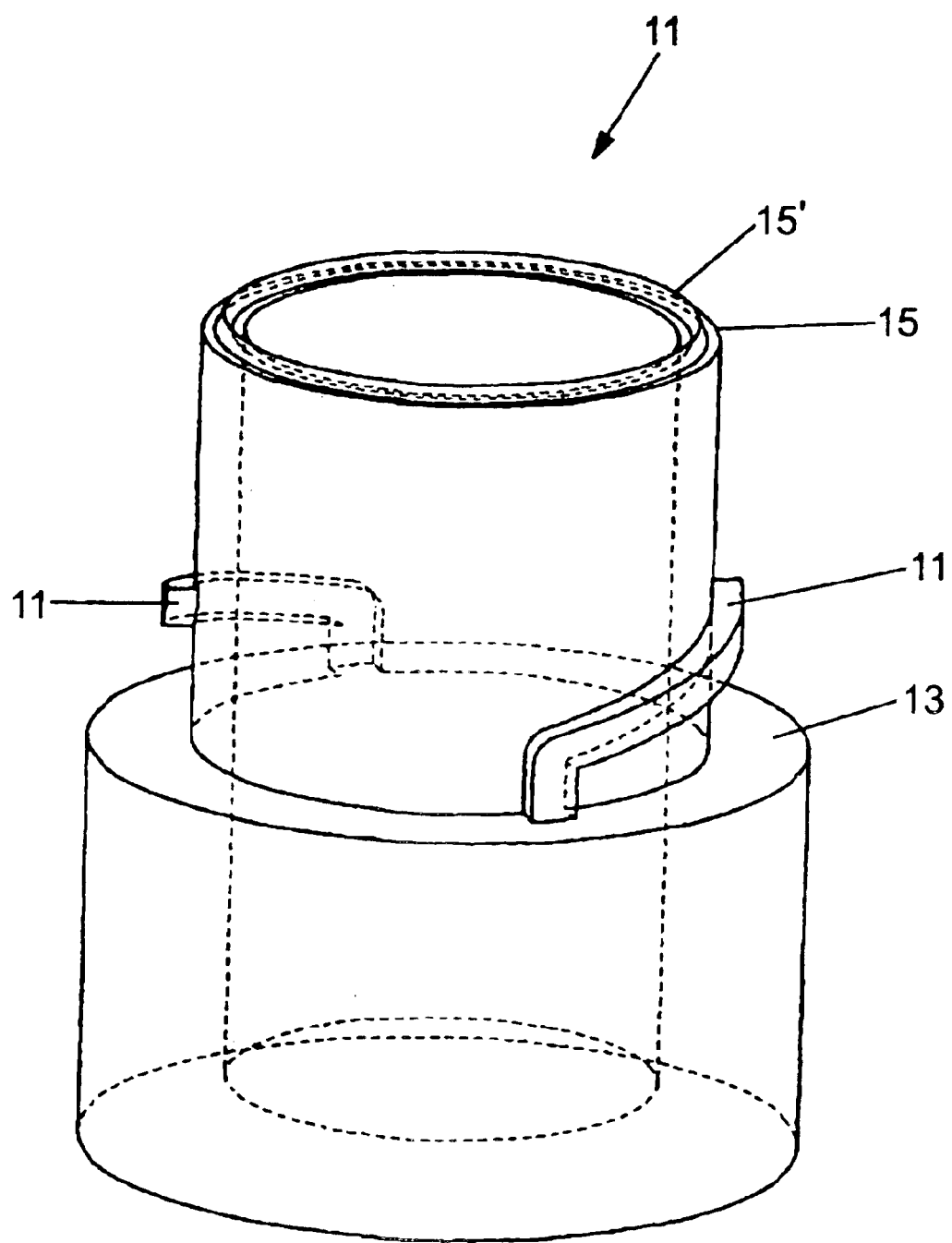
FIG. 5A shows an exemplary embodiment of a subject base having a sealing ridge poisoned on a sealing surface.
Figure 5B:
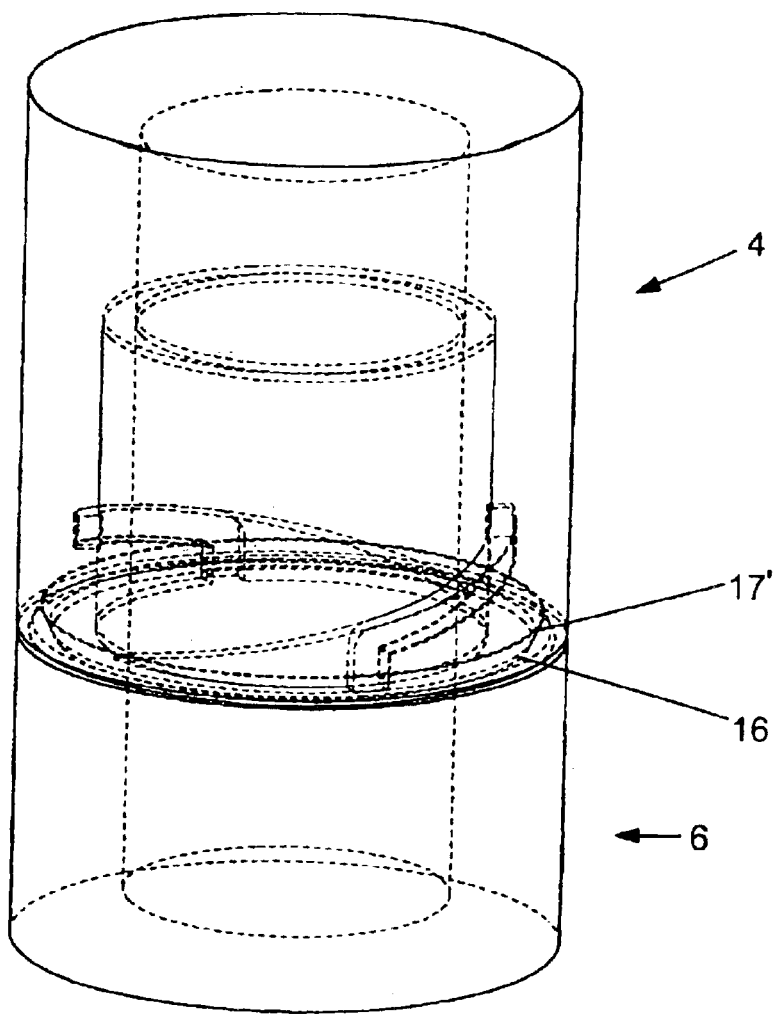
FIG. 5B shows an exemplary device according to the subject invention wherein the base and cover are mated together to form an intimate seal by way of at least corresponding threads and a sealing ridge and mated sealing groove such as sealing groove 16 of FIG. 5 and sealing groove 17' of FIG. 4.

FIG. 5A shows an exemplary base assembly 11, which is substantially similar to base assembly 6 of FIG. 5, except that it has a sealing ridge 15' positioned on a sealing surface other than sealing surface 13, i.e., sealing ridge 15' is positioned on sealing surface 15, which may be in addition to or in place of a sealing ridge positioned on another sealing surface such as ridge 16 positioned on sealing surface 13 of FIG. 5. As mentioned above, in all embodiments of the subject invention, the sealing ridges may instead be sealing grooves and vice versa.

Figure 5C:
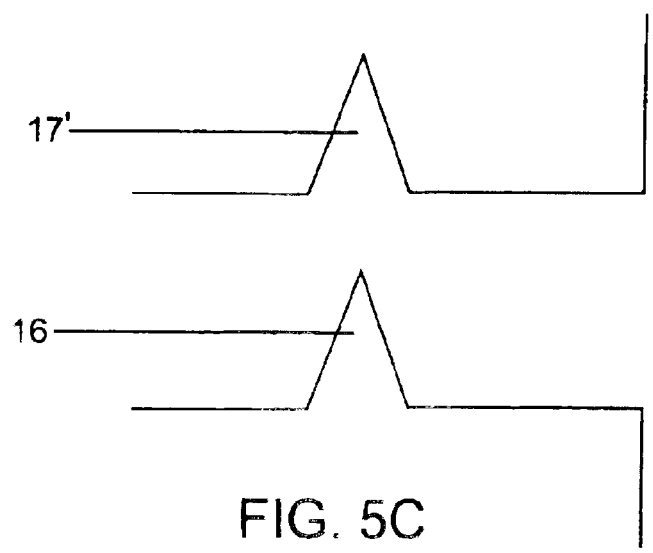
FIG. 5C shows a cross sectional view of an exemplary base having a sealing surface with a sealing ridge and an exemplary corresponding, mateable cover having a sealing surface with a sealing groove.

As described above, sealing ridge 16 and sealing ridge 15' are configured and dimensioned to correspond with a respective corresponding groove positioned on a cover assembly such that the groove on the cover assembly tightly receives the ridge 16 or 15' therein when mated together to form a snug fit. FIG. 5C shows a cross sectional view of the sealing surfaces of an exemplary base and cover having a sealing ridge and a corresponding groove. Accordingly, FIG. 5C shows a sealing ridge such as sealing ridge 16 of FIG. 5 (or sealing ridge 15' of FIG. 5A) and a corresponding cover having a mateable groove such as groove 17' of FIG. 4 (or groove 8' of FIG. 4B). As mentioned above, the ridge may be positioned on the cover and the mateable groove positioned on the base. The ridge is typically configured to have a substantially "V"-like shape, but other suitable shapes are, of course, possible.

Figure 6A:
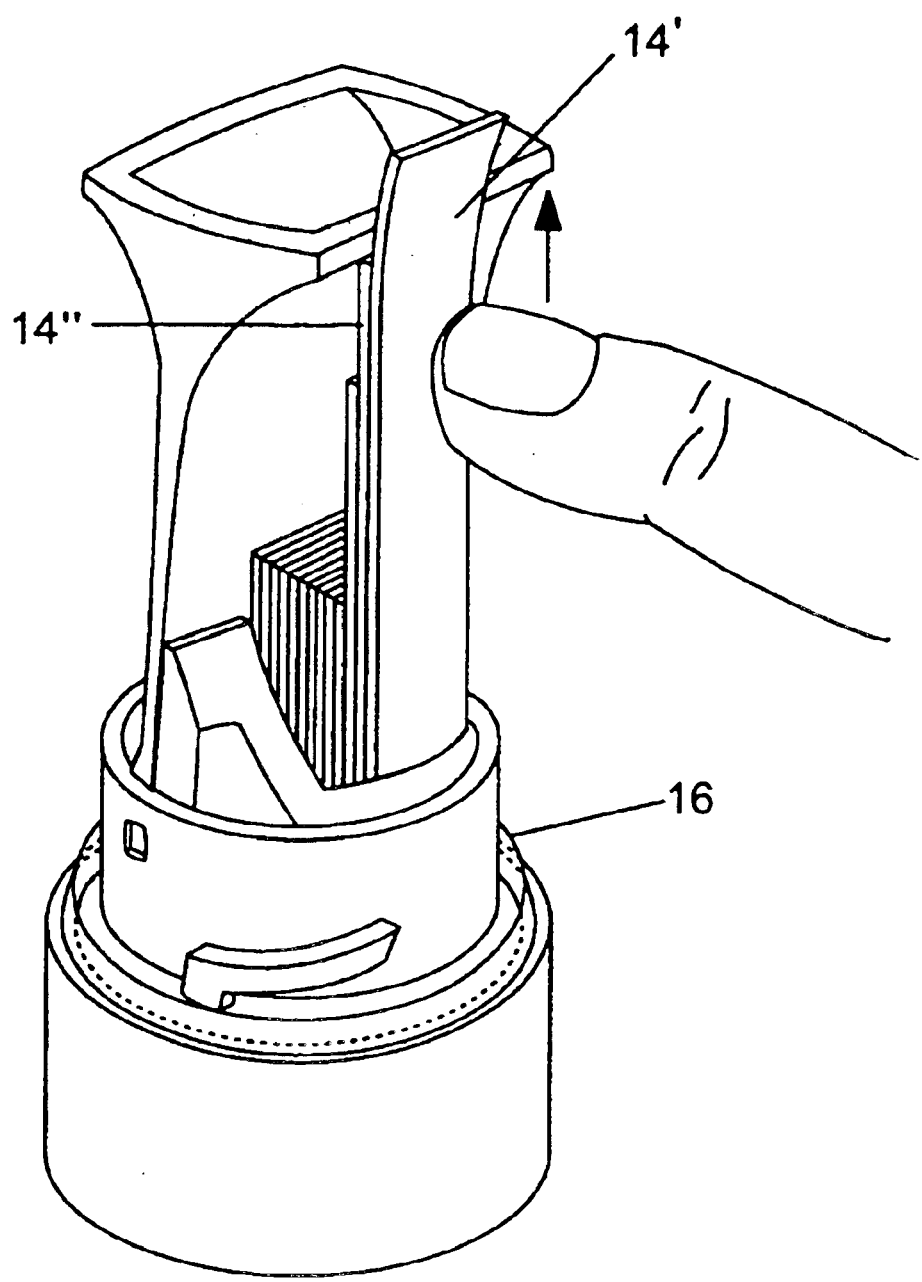

FIG. 6 shows yet another embodiment of an exemplary subject base assembly. Base assembly 6' is substantially similar to base assembly 6 of FIG. 5. However, base assembly 6' includes a test strip engagement element 22 which is configured to facilitate removal of a single test strip from a plurality of test strips stored in the housing. As mentioned above, the test strip engagement element 22 is also configured to prevent removal of any other test strip, i.e., it only enables single test strip removal. Accordingly, the test strip engagement element 22 includes a first lip extension 23 on a first side and a second lip extension 27 on a second side, both positioned at the distal end 25 of the test strip engagement element, where the lip extensions 23 and 27 are configured to allow a single test strip to slide or move along the surface of the engagement element, e.g., the lip extension, while catching any other test strip under the lip extension, as shown in FIG. 6A and as will be explained in greater detail below. In this particular embodiment, the engagement element 22 has two test strip engaging sides with respective lip extension 23 and 27; however fewer or greater than the illustrated number of sides and lip extensions may be present.

As also shown in FIG. 6, test strip stack 14 is positioned inside a test strip compartment 18, where such a compartment may be integral with the base or may be a separate piece and may also be readily removable for easy test strip re-filling. A similar test strip stack 14 and test strip compartment (not shown) may be positioned on the opposing side of the engagement element so as to be similarly associated with lip extension 27. Also present on the base assembly 6' is recess 19 which is configured to function as a lock-key attachment means when operatively associated with a corresponding protrusion on a test strip engagement element, such as protrusion 1 on test strip engagement element 28 of FIG. 6B.

FIG. 6B shows a full view of an exemplary test strip engagement element, similar to the test strip engagement element 22 of FIG. 6. In this embodiment, the proximal end 26 of test strip engagement element 28 includes a data storage element 29 and an electronic coupling means 21 for operatively coupling to an external or remote device and thus communicating or transferring data thereto.

Figure 7C:
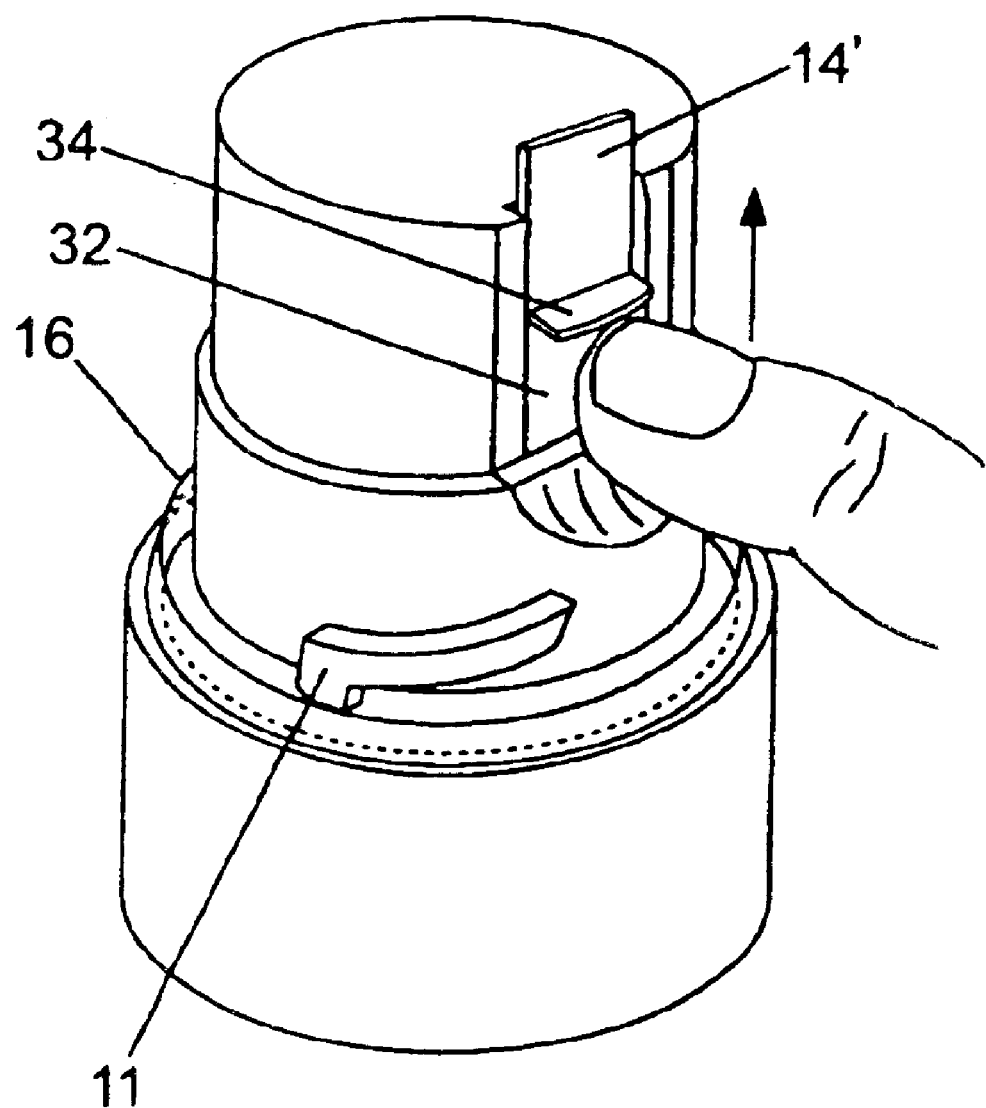
FIG. 7C shows an exemplary method of removing a single test strip, such as a test strip from the test strip dispenser of FIGS. 7A and 7B.

FIGS. 7 and 7A show another exemplary embodiment of the subject invention having a slideably associated test strip engagement element. FIG. 7 shows an exterior view of a base member 30 having a slideably associated test strip engagement element 32 associate therewith. A portion of test strip engagement element 32 is disposed within the base assembly, while handle 34 is positioned outside the base so as to be accessible to a user of the device. Test strip engagement element 32 is also associated with a stack of test strips such that it picks and advances or moves a single test strip, herein shown as test strip 14', distal to the base for removal (see FIG. 7C). As described above, the slideably associated test strip engagement element may be moved automatically or manually, for example by an individual engaging and moving the handle thereof.

FIG. 7B illustrates an exploded view of the association of test strip engagement element 32 with a test strip stack. As shown, the distal end of the test strip engagement element 32 includes a handle 34 attached to a connecting means or rod or plate mid section 33. The proximal end 35 of the test strip engagement element 32 includes at least one test strip grasping means, herein shown as two ledges or arms 36, where such grasping means are configured to grasp or engage edge E of an end or top most test strip 14' from a plurality or stack of test strips 14 and slideably move test strip 14' away or distally from the stack 14 so it can be easily grasped by an individual. As described above, test strip stack 14 may further be associated with an urging means 12, herein shown as a spring element 12, and a substantially planar, rigid plate 39 for maintaining the test strips together in a suitable orientation.

FIG. 7A shows an internal view (shown in phantom) of the base assembly 30 of FIG. 7. The phantom lines illustrate the recess 100 which retains the test strip stack 14 in the base. In other words, the base is configured to include a negative space dimensioned and configured to retain the plurality of test strips in the device. As shown in FIG. 7A, the recess 100 is also configured, i.e., a negative space is provided, to accommodate engagement element 32 and grasping means 36, e.g., recesses 36' are configured to accommodate grasping means 36.

Methods

Also provided by the subject invention are methods for dispensing a test strip from a plurality or stack of test strips. More specifically, methods are provided that enable a single test strip to be grasped easily, for example by a visually and/or dextrally impaired individual such as a visually and/or dextrally impaired diabetic and the like.

Accordingly, the first step is to provide a test strip dispenser, where such a dispenser is configured to store at least one and more likely a plurality of test strips, such as the test strip dispenser devices described above.

In one embodiment of the subject methods, a test strip is easily dispensed for use by exerting a first force upon the plurality of test strips, where such a first force urges the plurality of test strips together to facilitate the dispensing task. In such a method, a test strip is removed from the plurality of test strips by applying a second opposing force and slideably moving or advancing a test strip away from the plurality, e.g., in a direction distal to the plurality of test strips, where such a second force and subsequent movement may be accomplished manually or automatically, for example with a suitable test strip movement means, and will typically be accomplished manually, for example by a finger.

More specifically, a test strip dispenser is provided where the height of the base assembly or the portion that retains or stores the test strips is less than the height of each of the retained test strips, as described above, to provide easy access to a top most test strip while minimizing direct contact with other test strips. More specifically, the height of the base assembly is less than the length of each of the test strips retained therein, i.e., a portion of each of the retained test strips extends beyond the distal edge or top portion of the base assembly, where usually the portion of the test strip that extends beyond the base assembly is the contact or non-testing area of the test strip. For example, the height of the base assembly is typically at least about two thirds the length of each test strip (i.e., one third of each test strip protrudes above the distal edge of the base assembly), where the height of the base assembly may be as little as about one half or one quarter or less the length of each test strip, where exemplary dimensions for a cylindrically shaped device having a base assembly that has a height that is less than the length of each of the retained test strips are described above and will not be repeated here.

Figure 5D:
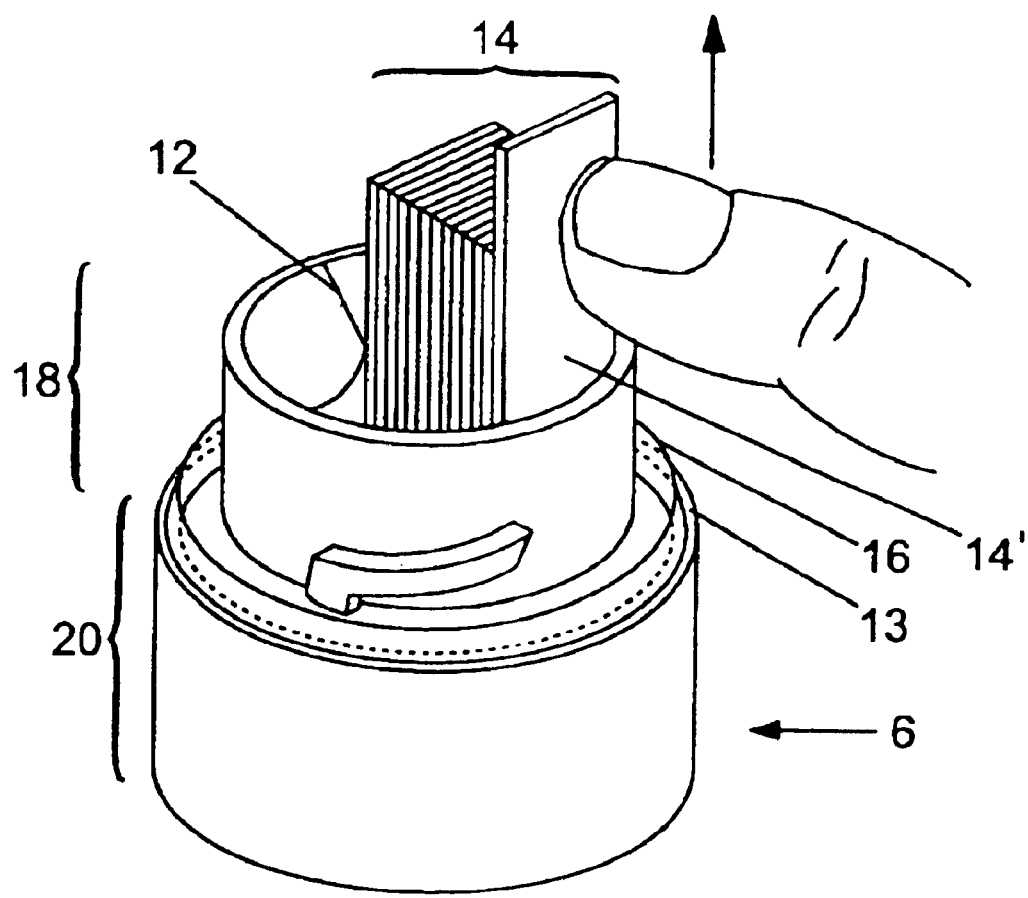
FIG. 5D shows an exemplary method of removing a single test strip from a subject base, such as base 6 of FIG. 5.

As such, FIG. 5D shows an exemplary method of removal of a single test strip from a subject base such as base 6 of FIG. 5. As illustrated in FIG. 5D, a first force is applied by, for example, an urging means 12, to a first end of the plurality of test strips 14. A test strip movement means, e.g., finger or other test strip movement means (manual or automatic), applies a second force to the opposite end of the test strip stack, i.e., to the top most test strip 14' to be removed from the plurality, and moves the test strip 14' in a direction, e.g., distal direction, away from the plurality. Typically, the portion of the test strip contacted by a finger or the like will be a portion suitable for handling, i.e., a contact area such as a non-testing or non-reaction area. In certain embodiments, the plurality of test strips is further held together by a rigid plate or the like, as described above, where such a plate also minimizes the chances that the test strips will inadvertently fall out of the dispenser. As will be apparent, this particular embodiment provides an easy method of accessing a single test strip without the need of a device having complex, multiple, moveable parts. Furthermore, in this particular embodiment, it will be apparent that the test strips need not be stacked in a precise manner, but rather each strip need only be positioned behind another in some fashion. As such, ease of manufacturing and use are increased.

In another embodiment of the subject methods, a test strip is removed from a plurality or stack of test strips by moving, either automatically or manually with a finger, the test strip along or adjacent a lip extension, where such a lip extension serves to remove a single test strip from a plurality of test strips while also preventing removal of any other test strip, i.e., it only enables single test strip removal by providing a simple method of segregating a single test strip from the plurality of test strips. Accordingly, a test strip is advanced or moved by a test strip movement means (i.e., an automatic movement means or manual movement means such as a finger) adjacent a lip extension while other, remaining test strips are caught or retained under the lip extension and thus prevented from being removed. This particular embodiment also provides an easy method of accessing a single test strip without the need of a device having complex, multiple, moveable parts.

More specifically, a test strip engagement element having a lip extension, such as described above, is provided. As shown in FIG. 6A, a finger or other means, e.g., automatic means, engages a test strip, i.e., engages a top most test strip 14' from the plurality of test strips stored in the dispenser, for removal. Typically, the portion of the test strip contacted by a finger or the like will be a portion suitable for handling, i.e., a contact areas such as a non-testing or non-reaction area. Once a test strip is engaged with a finger or other movement means, the engaged test strip is advanced or moved in a direction, i.e., a distal direction as shown by the arrow, away from the plurality of test strips, where it is advanced adjacent the lip extension and further segregated from the plurality so that it can be easily grasped and removed for use. As shown in FIG. 6A, any and all other test strips, such as test strip 14" which may have also been somewhat advanced, are prevented from further advancement by engagement with an area under the lip extension. Similar to the embodiment described above, it will be apparent that the test strips need not be stacked in a precise manner in this embodiment, but rather each strip need only be positioned behind another in some fashion. As such, ease of manufacturing and use are increased.

In certain other embodiments of the subject methods, a test strip, i.e., an end or top most test strip is engaged by a grasping means and advanced or moved in a direction, i.e., a distal direction, away from the plurality of test strips so that it may be easily grasped.

More specifically, a test strip engagement element having a grasping means, such as described above, engages a test strip, either manually or automatically, and advances the test strip away from the remaining test strips (see FIG. 7C which shows such an exemplary method of removing a single test strip, such as a method of removing a single test strip from the test strip dispenser of FIGS. 7A and 7B). For example, one or more ledges, teeth or arms grasps an end or edge of a top most test strip and distally move the test strip in a direction away from the test strip stack, where the grasping means may grasp and move a test strip manually, e.g., move a test strip by a finger or the like, or automatically by a suitable movement means. In addition to, or in place of, the above described method of advancing a test strip by engaging it with one or more ledges, teeth or arms, the test strip may also be grasped or engaged by a magnet means, an adhesive, a coating layer or pattern associated with the test strip engagement element. In certain embodiments, the magnet means, adhesive, coating layer or pattern may be associated with the test strip, as well as or in addition to, the test strip engagement element.

As mentioned above, the test strips of the plurality of test strips may further be urged together, for example on a side opposite the engagement element, to better enable grasping by the grasping means (see for example FIG. 7B). Once the top most test strip is removed from the plurality, i.e., removed from the test strip dispenser, the process may then be repeated for the next sequential test strip or current, top most test strip.

Also provided are methods for creating and maintaining a substantially air and moisture tight seal of a test strip dispenser, where such a seal protects the moisture sensitive test strips stored in a test strip dispenser. By substantially air and moisture tight seal is meant that the housing is capable of preventing substantial air and/or moisture from entering the housing when the housing is in a closed position. In other words, when in a mated configuration, the inside of the housing is a substantially air tight and moisture free environment and more specifically the test strips inside the housing are in a substantially air tight and moisture free environment when the housing is in a closed configuration. One or more of the below described methods for accomplishing a substantially air and moisture free housing seal may be employed.

In one particular embodiment of the subject methods, the substantially air and moisture tight seal is accomplished by threadably engaging the cover and base assemblies of the test strip dispenser device. Specifically, a cover assembly is provided with a thread positioned on the cover, such as on the inside of a substantially circular or cylindrical cover and a base assembly is provided with a corresponding thread, for example positioned on the outside of the base. The cover and base assemblies are aligned or mated together to form a closed dispenser, typically the cover will encompass a portion of the base such that a portion of the base, i.e., the area of the base having a thread, is inside the cover so as to create a flush housing exterior. Accordingly, the corresponding threads are threaded together, e.g., by a ¼ turn, ½ turn, ¾ turn or even a full turn or two or more turns, or the like, to associate the threads of the cover and base together to create a substantially air and moisture tight seal. As noted above, threadably engaging the assemblies advantageously allows a small hand torque to create a large or substantial sealing pressure or force on the sealing surfaces to create a tight seal therebetween.

In another embodiment, a substantially air and moisture tight seal is accomplished by intimately seating the base assembly into the cover assembly, i.e., frictionally engaging the cover and base assemblies together. For example, a seating mechanism, as described above, may be employed to form an intimate contact between the base and cover assemblies. More specifically, one or more protrusions positioned on the inside the cover is mated adjacent a distal edge or ledge of the base assembly, where such a mating forms an intimate seal, i.e., a substantially air and moisture proof seal.

In addition to, or in place of, other described methods for creating and maintaining a substantially air and moisture tight seal, an O-ring gasket may be employed to form an intimate contact between the base and cover assemblies. For example, an O-ring may be positioned on the cover or the base to form an intimate contact when the cover and base are in a closed position.

Still further, a lock and key mechanism may be employed. For example, a protrusion on the inside cover is aligned and mated with a corresponding groove on the base, or vice versa, securing the assemblies in an intimately contacted configuration. To separate the two assemblies, one of the assemblies is urged away from the other to "unlock" the protrusion from the groove. For example, a tab or lip may be provided on the cover assembly adjacent a protrusion, e.g., on the outside of the cover assembly. Engaging the tab disengages the protrusion or rather moves the protrusion out of its corresponding groove on the base assembly. However, other means for "unlocking" the mechanism may, of course, also be employed.

In another embodiment, a method employing a tensioning clamp similar to that which is used to fasten and close ski boots (see for example U.S. Pat. No. 6,145,168, the disclosure of which is herein incorporated by reference) may be used to create a substantially air and moisture tight seal. Accordingly, a cover and base are brought into a closing position and a gripping arm on, for example the outside of the cover, is caused to interact with one of a plurality of teeth, for example positioned on the outside of the base. A tension is created, i.e., a force is applied, by moving an actuating arm operatively associated with the gripping arm, bringing the cover and base closer together to form a close, intimate contact which is substantially air and moisture impenetrable.

In certain embodiments of the subject methods, the substantially air and moisture tight seal is effected and maintained by mating or tightly fitting or positioning a sealing ridge of a first assembly as described above (i.e., a first assembly such as a base assembly) with a corresponding groove on the second assembly (i.e., a cover in this particular example). As such, the receiving groove positioned on a sealing surface of an assembly such as a cover assembly receives a corresponding sealing ridge positioned on a mateable assembly such as a base assembly, where such groove/ridge interaction provides a substantially air and moisture tight seal between the base and cover assemblies when they are in a closed configuration.

Kits

Finally, kits for practicing the subject methods are provided. The subject kits at least include one or more test strip dispensing devices of the subject invention. Oftentimes, a plurality of subject devices is included. The subject kits may also include one or more test strips, usually a plurality of test strips. The kits may further include a meter for automatically determining the presence and/or concentration of at least one analyte in a physiological sample applied to a test strip. Finally, the kits may further include instructions for using the subject devices for dispensing test strips and may also include instruction for determining the presence and/or concentration of at least one analyte in a physiological sample applied to a test strip. The instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g., CD-ROM, diskette, etc.

It is evident from the above description and discussion that the above described invention provides a simple, quick and convenient way to dispense test strips. The above described invention provides a number of advantages, including, but not limited to, ease and low cost manufacture, portability, ease of use, particularly for visually and dextrally impaired individuals, and minimal test strip damage from light, humidity, and other environmental contaminants including oils and the like from a user's hands. As such, the subject invention represents a significant contribution to the art.

The subject invention is shown and described herein in what is considered to be the most practical, and preferred embodiments. It is recognized, however, that departures may be made therefrom, which are within the scope of the invention, and that obvious modifications will occur to one skilled in the art upon reading this disclosure.

The specific devices and methods disclosed are considered to be illustrative and not restrictive. Modifications that come within the meaning and range of equivalents of the disclosed concepts, such as those that would readily occur to one skilled in the relevant art, are intended to be included within the scope of the appended claims.

What is claimed is:

1. A device for storing at least one test strip and dispensing a single test strip at a time, said device comprising:
   a housing comprising:
   (a) a cover; and
   (b) a base configured to store a plurality of test strips, wherein the height of said base is less than the length of each of the test strips, such that a portion of each of the test strips stored in said base extends beyond the height of said base, wherein said device further comprises a surface having a sealing ridge and surface having a sealing groove mateable with said sealing ridge to provide a substantially air and moisture tight seal when said sealing ridge and said sealing groove are mated together.

2. The device according to claim 1, wherein when said at least one test strip is stored in said device, said height of said base is at least about two thirds of the length of each of the test strips stored in said device.

3. The device according to claim 1, wherein said base further comprises an urging element for applying a force to the stored test strips when stored in said device.

4. The device according to claim 3, wherein said urging element is selected from the group consisting of sponge, foam, a spring and a plunger.

5. The device according to claim 1, wherein said base further comprises a substantially planar, rigid plate for maintaining test strips stored in said device in a suitable orientation for dispensing.

6. The device according to claim 1, wherein said housing comprises at least one attachment means configured to mate said cover with said base.

7. The device according to claim 6, wherein said at least one attachment means is at least one of a threading means, an O-ring gasket, a lock and key mechanism, a tensioning clamp and a snap fit mechanism.

8. The device according to claim 1, wherein said base further comprises a test strip engagement element configured to dispense a single test strip at a time from said housing when at least one test strip is stored in said device.

9. The device according to claim 8, wherein said test strip engagement element comprises at least one lip extension configured to separate the single test strip from said plurality of stored test strips.

10. The device according to claim 8, wherein said test strip engagement element comprises at least one grasping means for grasping a single test strip at a time when at least one test strip is stored in said device.

11. The device according to claim 1, wherein said base further comprises a test strip segregation means.

12. The device according to claim 11, wherein said test strip segregation means is positioned on a bottom wall of said base and is at least one of an apex, pattern and a protrusion.

13. The device according to claim 1, wherein said cover and said base are two, separate pieces.

14. The device according to claim 1, wherein said device is configured to enable a threadable engagement of said cover to said base.

* * * * *